United States Patent [19]

Arima et al.

[11] Patent Number: 5,247,067
[45] Date of Patent: Sep. 21, 1993

[54] PEPTIDE AND ITS USE

[75] Inventors: Terukatsu Arima, 5-1, Hirano-cho, Kagoshima-shi, Kagoshima-ken; Kyoko Yamada, Kurashiki; Tadashi Hatanaka, Kurashiki; Toshihiko Namba, Kurashiki; Masao Tsuji, Kurashiki, all of Japan

[73] Assignees: Kuraray Co., Ltd., Kurashiki; Terukatsu Arima, Kagoshima, both of Japan

[21] Appl. No.: 666,719

[22] Filed: Mar. 8, 1991

[30] Foreign Application Priority Data

Mar. 8, 1990 [JP] Japan ................................. 2-58700
Mar. 16, 1990 [JP] Japan ................................. 2-67439
Mar. 27, 1990 [JP] Japan ................................. 2-80100
Oct. 31, 1990 [JP] Japan ................................. 2-296899

[51] Int. Cl.$^5$ .................... A61K 37/02; G01N 30/96
[52] U.S. Cl. .................... 530/324; 422/61; 530/806
[58] Field of Search ............. 530/324, 325, 326, 327, 530/328, 329, 330, 806; 514/15, 16, 17; 422/61

[56] References Cited

FOREIGN PATENT DOCUMENTS 0318216 5/1989 European Pat. Off. .
8403564 9/1984 World Int. Prop. O. .

OTHER PUBLICATIONS

J. Immun. Meth. vol. 102 (1987) pp. 259–274.
Arima et al. Gastro. Jap. vol. 25, No. 2 Apr. 1990 218–222.
Mehra et al. PNAS vol. 83, 7013–7017 (Sep. 1986).
Choo et al, *Science,* vol. 244, pp. 359–362 (1989).
Kuo et al, *Science,* vol. 244, pp. 362–364 (1989).
Arima et al, *Gastroenterologia Japonica,* vol. 24, No. 5, pp. 540–544; 545–548 (1989).
Chemical Abstracts, 277951y, vol. 115, Aug. 21, 1991, & EP-A-0 442 394, C. Y. Wang, "Synthetic Peptides for the Detection of Antibodies to Hepatitis C Virus (HCV), Diagnosis of HCV Infection, and Prevention Thereof as Vaccines".

*Primary Examiner*—Merrell C. Cashion, Jr.
*Assistant Examiner*—Bennett Celsa
*Attorney, Agent, or Firm*—Oblon, Spivak, McClelland, Maier & Neustadt

[57] ABSTRACT

The present invention relates to a peptide having the amino acid sequence: Lys Arg Ser Thr Asn, Arg Arg Tyr Lys Glu Lys Glu Lys or Ala Ile Ile Pro Asp Arg Glu Val Leu Tyr and which peptide is capable of specifically binding to the antibody which is specific to the non-A, non-B hepatitis associated antigen. The peptide can be used as an anti-HCV antibody assay reagent with high sensitivity.

2 Claims, 15 Drawing Sheets

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Lys Asp Arg Thr Gln Gln Arg Lys Thr Lys Arg Ser Thr Asn Arg Arg
1               5                   10                  15

Arg Ser Lys Asn Glu Lys Lys Lys Lys
            20              25
```

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Lys Arg Ser Thr Asn
1               5
```

( 2 ) INFORMATION FOR SEQ ID NO:3:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Glu Lys Lys Gly Glu Ala Ser Asn Gly Glu Ala Glu Asn Asp Thr His
1               5                   10                  15

Lys Lys Gln Arg Arg Tyr Lys Glu Lys Glu Lys Thr Ala Thr Asn Asn
            20              25                  30

Pro Gly Lys Asn Lys Lys Pro Arg
            35              40
```

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Arg Arg Tyr Lys Glu Lys Glu Lys
1               5
```

( 2 ) INFORMATION FOR SEQ ID NO:5:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Arg Val Val Leu Ser Gly Lys Pro Ala Ile Ile Pro Asp Arg Glu Val
1               5                   10                  15
Leu Tyr Arg Glu Phe Asp Glu Met Glu Cys Ser Gln His Leu Pro
            20              25                  30
Tyr Ile Glu Gln Gly Met Met
        35
```

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Ala Ile Ile Pro Asp Arg Glu Val Leu Tyr
1               5                   10
```

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Thr Lys Arg Ser Thr Asn Arg Arg Arg Ser
1               5                   10
```

( 2 ) INFORMATION FOR SEQ ID NO:8:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Arg Arg Tyr Lys Glu Lys Glu Lys Thr Ala Thr Asn Asn Pro Gly Lys
1               5                   10                  15
Asn Lys Lys Pro Arg
            20
```

( 2 ) INFORMATION FOR SEQ ID NO:9:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Thr His Lys Lys Gln Arg Arg Tyr Lys Glu Lys Glu Lys
1               5                   10
```

( 2 ) INFORMATION FOR SEQ ID NO:10:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:10:

Arg Arg Tyr Lys Glu Lys Glu Lys Thr Ala
1               5                   10

( 2 ) INFORMATION FOR SEQ ID NO:11:

( i ) SEQUENCE CHARACTERISTICS:
    ( A ) LENGTH: 31 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:11:

Ala Ile Ile Pro Asp Arg Glu Val Leu Tyr Arg Glu Phe Asp Glu Met
1               5                   10                  15

Glu Glu Cys Ser Gln His Leu Pro Tyr Ile Glu Gln Gly Met Met
            20                  25                  30

( 2 ) INFORMATION FOR SEQ ID NO:12:

( i ) SEQUENCE CHARACTERISTICS:
    ( A ) LENGTH: 18 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:12:

Arg Val Val Leu Ser Gly Lys Pro Ala Ile Ile Pro Asp Arg Glu Val
1               5                   10                  15

Leu Tyr ( 2 ) INFORMATION FOR SEQ ID NO:13:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:13:

Ala Ile Ile Pro Asp Arg Glu Val Leu Tyr
1               5                   10

( 2 ) INFORMATION FOR SEQ ID NO:14:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:14:

Lys Asp Arg Thr Gln Gln Arg Lys Thr Lys
1               5                   10

( 2 ) INFORMATION FOR SEQ ID NO:15:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:15:

```
Arg Ser Thr Asn Arg Arg Arg Ser Lys Asn Glu Lys Lys Lys Lys
1               5                   10                  15
```

( 2 ) INFORMATION FOR SEQ ID NO:16:

( i ) SEQUENCE CHARACTERISTICS:
    ( A ) LENGTH: 32 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:16:

```
Glu Gln Asp Gln Ile Leu Thr Lys Asp Arg Thr Gln Gln Arg Lys Thr
1               5                   10                  15

Lys Arg Ser Thr Asn Arg Arg Arg Ser Lys Asn Glu Lys Lys Lys Lys
                20                  25                  30
```

( 2 ) INFORMATION FOR SEQ ID NO:17:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:17:

```
Glu Lys Lys Gly Glu Ala Ser Asn Gly Glu Ala Glu Asn Asp
1               5                   10
```

( 2 ) INFORMATION FOR SEQ ID NO:18:

( i ) SEQUENCE CHARACTERISTICS:
    ( A ) LENGTH: 11 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:18:

```
Thr Asn Asn Pro Gly Lys Asn Lys Lys Pro Arg
1               5                   10
```

( 2 ) INFORMATION FOR SEQ ID NO:19:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:19:

```
Val Gly Arg Ile Lys Asn Trp Asn Arg Glu Gly Arg Lys Asp Ala Tyr
1               5                   10                  15

Gln Ile Arg Lys Arg
                20
```

( 2 ) INFORMATION FOR SEQ ID NO:20:

(i) SEQUENCE CHARACTERISTICS:
  (A) LENGTH: 11 amino acids
  (B) TYPE: amino acid
  (D) TOPOLOGY: linear (ii) MOLECULE TYPE: peptide (xi) SEQUENCE DESCRIPTION: SEQ ID NO:20:

```
Arg Val Val Leu Ser Gly Lys Pro Ala Ile Ile
 1           5                      10
```

(2) INFORMATION FOR SEQ ID NO:21:

(i) SEQUENCE CHARACTERISTICS:
    (A) LENGTH: 120 base pairs
    (B) TYPE: nucleic acid
    (C) STRANDEDNESS: unknown
    (D) TOPOLOGY: unknown (ii) MOLECULE TYPE: cDNA (iii) HYPOTHETICAL: NO (vi) ORIGINAL SOURCE:
    (A) ORGANISM: Homo sapiens
    (F) TISSUE TYPE: serum (vii) IMMEDIATE SOURCE:
    (B) CLONE: #oft Corp (xi) SEQUENCE DESCRIPTION: SEQ ID NO:21:

```
GAATTCCAAA AAGAGCAAAA CAAACCGCCG AAGAAAAAAC TAATAAGAGA AGAAAAGGCG      60

AAGAGACACA GGAAAAAAAA AACAGAGACG AAGGTCAGAT AGAAAAAAAG CAAGGAATTC     120
```

(2) INFORMATION FOR SEQ ID NO:22:

(i) SEQUENCE CHARACTERISTICS:
    (A) LENGTH: 114 base pairs
    (B) TYPE: nucleic acid
    (C) STRANDEDNESS: unknown
    (D) TOPOLOGY: unknown (ii) MOLECULE TYPE: cDNA (iii) HYPOTHETICAL: NO (vi) ORIGINAL SOURCE:
    (A) ORGANISM: Homo sapiens
    (F) TISSUE TYPE: serum (vii) IMMEDIATE SOURCE:
    (B) CLONE: #Microsoft Corp (xi) SEQUENCE DESCRIPTION: SEQ ID NO:22:

```
GAATTCCGAG AACAAGACCA GATAAAAACC AAAGACAGAA CACAACAGAG AAAGACGAAA      60

AGAAGCACCA ATCGCAGGCG AAGCAAAAAC GAAAAAAAAA AAAAAAGGA ATTC            114
```

(2) INFORMATION FOR SEQ ID NO:23:

(i) SEQUENCE CHARACTERISTICS:
    (A) LENGTH: 201 base pairs
    (B) TYPE: nucleic acid
    (C) STRANDEDNESS: unknown
    (D) TOPOLOGY: unknown (ii) MOLECULE TYPE: cDNA (iii) HYPOTHETICAL: NO (vi) ORIGINAL SOURCE:
    (A) ORGANISM: Homo sapiens
    (F) TISSUE TYPE: serum (vii) IMMEDIATE SOURCE:
 (B) CLONE: #Microsoft Corp (xi) SEQUENCE DESCRIPTION: SEQ ID NO:23:

```
GAATTCCAAG  AAAAAAGGG   AGAAGCCAGC  AATGGAGAAG  CCGAAAACGA  CACACACAAG   60
AAACAAAGGA  GGTACAAAGA  AAAAGAAAAA  ACGGCAACAA  ATAACCCAGG  AAAGAACAAA  120
AAGCCAAGAG  TGGGCAGAAT  AAAAAACTGG  AACCGGGAGG  GAAGGAAGGA  CGCATATCAG  180
ATTAGAAAAA  GGAGGGAATT  C                                               201
```

PEPTIDE AND ITS USE

BACKGROUND OF THE INVENTION

1. Field of the Invention

The present invention relates to a peptide and its use.

The peptide provided by the present invention can be used for anti-HCV antibody assay, since it is capable of highly specifically binding to the antibody which is specific to the non-A, non-B hepatitis associated antigen (hereinafter referred to as HCV-associated antigen) (this antibody is hereinafter referred to as anti-HCV antibody).

The anti-HCV antibody assay reagent provided by the present invention is capable of detecting the anti-HCV antibody in serum or plasma with high sensitivity and useful in anti-HCV antibody assay.

2. Description of the Prior Art

At present, five viruses are known to cause viral hepatitis, which accounts for the majority of liver diseases, and are called hepatitis A virus, hepatitis B virus, hepatitis C virus, hepatitis D virus, and hepatitis E virus, respectively. Of these five types of viral hepatitis, hepatitis A and hepatitis E are orally infected, i.e., their infection is transient and does not become chronic. On the other hand, hepatitis B and hepatitis C become chronic by persistent infection and progress to cirrhosis or liver cancer at high probabilities, thus posing a major problem. With respect to hepatitis A, hepatitis B and hepatitis D, respective causative viruses have been detected, and it is now possible to make immunological diagnosis of these types of hepatitis. Also, the gene of hepatitis E virus is reported to have recently been isolated. The causative virus of post-transfusion non-A, non-B hepatitis (hereinafter referred to as PTNANBH) remained unknown despite much work by a large number of researchers before 1988, when the research group of Chiron Corporation in the United States succeeded in isolating and identifying the gene of PTNANBH virus from plasma of PTNANBH-infected chimpanzees [Science, vol. 244, p. 359 (1988) and Science, vol. 244, p. 362 (1988)], which virus was named hepatitis C virus (hereinafter abbreviated HCV). A deduced partial base sequence of this gene is already known [European Patent No. 0318216], which permits anti-HCV antibody detection and makes serologic diagnosis of HCV infection possible.

Also, it is reported that a ribonucleic acid which is assumed to be the gene of the causative virus of PTNANBH was isolated and identified from a PTNANBH patient by several researchers including one of the present inventors [Gastroenterologia Japonica, vol. 24, No. 5, p. 540 (1989); Gastroenterologia Japonica, vol. 24, No. 5, p. 545 (1989); and Naika, vol. 64, No. 6, p. 1022 (1989)].

It has been the common practice to make judgment for the presence or absence of anti-HCV antibody by an antigen-antibody reaction using λ phage as a means of screening of the desired cDNA from cDNA library. However, this immunoscreening method provides no quantitative information, and sometimes involve a reaction with a nonspecific antigen component in the Escherichia coli expression product. At present, anti-HCV antibody detection reagents based on enzyme immunoassay using an antigenic protein expressed by cloning the gene of HCV, incorporating it into a phage and using a yeast as the host are under development [Naika, vol. 64, No. 6, p. 1027 (1989)]. Also under development are the particle aggregation method based on the nature of gelatin particles sensitized with virus or its antigen component to aggregate in the presence of an antiviral antibody and the bead method which uses beads coated with virus or its antigen component for enzyme immunoassay.

In the conventional enzyme immunoassay method using an HCV-associated antigen, the anti-HCV antibody positive response rate is about 75% even among the subjects of assay with a clinical diagnosis of PTNANBH, i.e., PTNANBH which is negative for anti-HCV antibody occurs in a ratio of about 25%. Also, in the enzyme immunoassay method described above, the positive response rate is about 1% when the subjects of assay are normal humans, whereas the statistically obtained HCV infection rate is about 3%, i.e., about 2% specimens positive for anti-HCV antibody are overlooked. This fact demonstrates that some carriers are overlooked in HCV carrier screening of blood donors, and the ratio of prevention of transfusion of blood contaminated with non-A, non-B hepatitis virus is not always high. On the other hand, the antigenic protein expressed by cloning the gene of HCV, incorporating it in a phage and using a yeast as the host contains various nonspecific antigen components; therefore, if this antigen protein is used as a reagent for anti-HCV antibody assay, the reagent will reeognize not only the anti-HCV antibody in the sample but also nonspecific antibody components other than the anti-HCV antibody, which means that the assay results do not always exactly reflect the presence of anti-HCV antibody. As stated above, the conventional enzyme immunoassay method using an HCV-associated antigen do not permit us to accurately detect the anti-HCV antibody.

SUMMARY OF THE INVENTION

It is an object of the present invention to provide a peptide capable of specifically binding to anti-HCV antibody. It is another object of the present invention to provide an assay reagent for anti-HCV antibody.

The present inventors discovered a peptide capable of specifically binding to an antibody specific to the non-A, non-B hepatitis associated antigen out of the peptide fragments selected from polypeptides encoded by the PTNANBH-associated gene, and developed the present invention.

The objects described above can be accomplished by providing a peptide capable of specifically binding to an antibody specific to an HCV-associated antigen containing the amino acid sequence:

Lys Arg Ser Thr Asn (SEQ ID NO: 2),

Arg Arg Tyr Lys Glu Lys Glu Lys (SEQ ID NO: 4), or

Ala Ile Ile Pro Asp Arg Glu Val Leu Tyr (SEQ ID NO: 6).

Specifically, the peptide of the present invention are peptides having the amino acid sequences represented by the formula (I):

(SEQ ID NO: 1)
Lys Asp Arg Thr Gln Gln Arg Lys Thr Lys Arg Ser Thr
Asn Arg Arg Arg Ser Lys Asn Glu Lys Lys Lys Lys or a peptide comprising its fragment, which peptide has the amino acid sequence:

Lys Arg Ser Thr Asn  (SEQ ID NO: 2)

and which peptide is capable of specifically binding to an antibody specific to HCV-associated antigen; formula (II):

(SEQ ID NO: 3)
Glu Lys Lys Gly Glu Ala Ser Asn Gly Glu Ala
Glu Asn Asp Thr His Lys Lys Gln Arg Arg Tyr
Lys Glu Lys Glu Lys Thr Ala Thr Asn Asn Pro
Gly Lys Asn Lys Lys Pro Arg or a peptide comprising its fragment, which peptide has the amino acid sequence:

Arg Arg Tyr Lys Glu Lys Glu Lys  (SEQ ID NO: 4)

and which peptide is capable of specifically binding to an antibody specific to HCV-associated antigen; and formula (III):

(SEQ ID NO: 5)
Arg Val Val Leu Ser Gly Lys Pro Ala Ile Ile
Pro Asp Arg Glu Val Leu Tyr Arg Glu Phe
Asp Glu Met Glu Glu Cys Ser Gln His Leu
Pro Tyr Ile Glu Gln Gly Met Met or a peptide comprising its fragment, which peptide has the amino acid sequence:

Ala Ile Ile Pro Asp Arg Glu Val Leu Tyr  (SEQ ID NO: 6)

and which peptide is capable of specifically binding to an antibody specific to HCV-associated antigen.

The objects can be accomplished by providing an assay reagent for anti-HCV antibody comprising the peptide described above.

Figure 1:
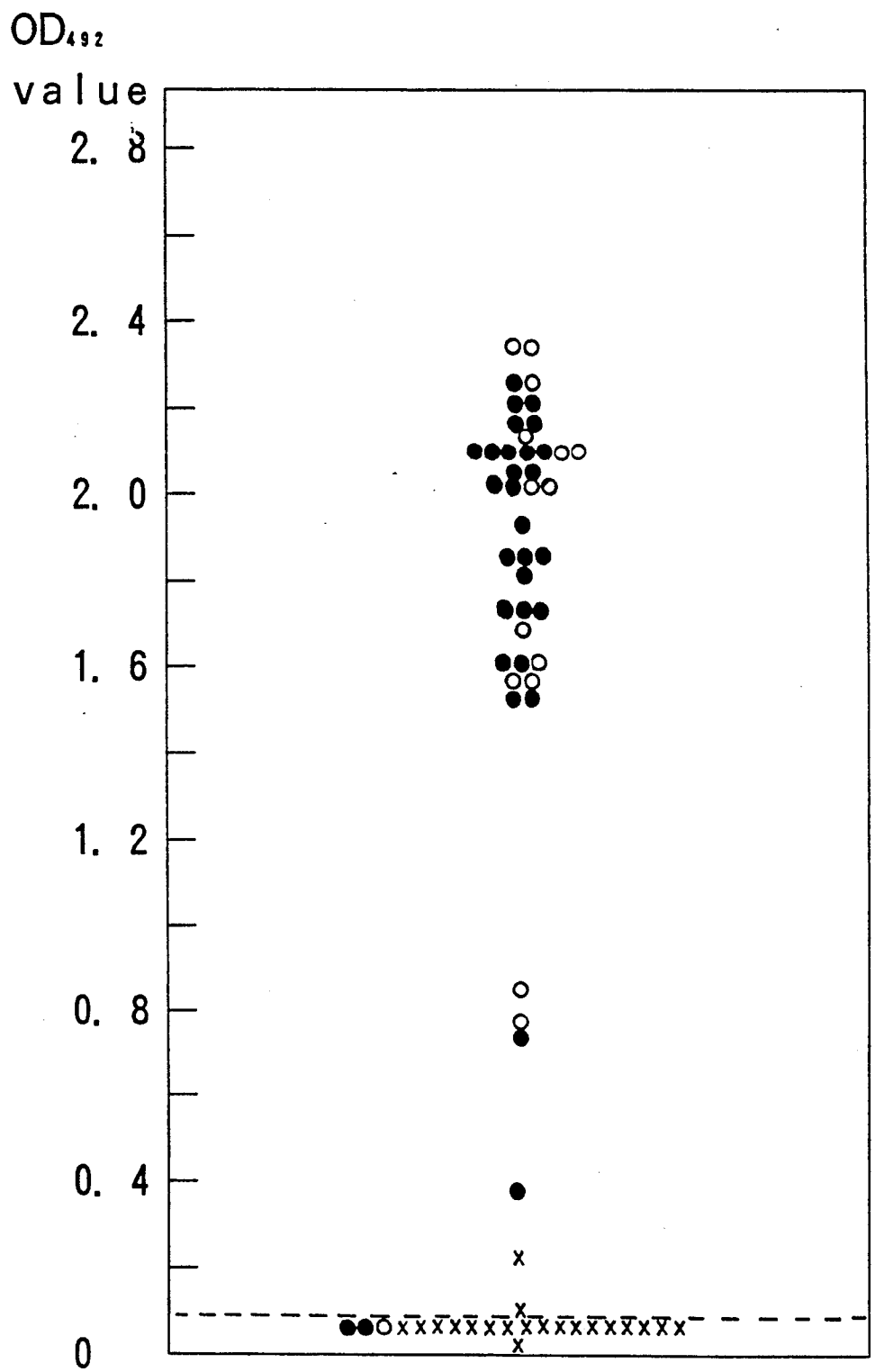
FIGS. 1, 2, 3, 4 and 5 show the $OD_{492}$ value distributions obtained by assaying respective serum specimens by the method described in Example 9 using the peptides obtained in Examples 1 and 2 and Reference Examples 1, 2 and 3, respectively.

The symbols used in these figures denote the following:

● $D_{492}$ value from GPT > 200 IU; HBsAg(−) serum A

○: $OD_{492}$ value from GPT > 200 IU; HBsAg(−) serum B x: $OD_{492}$ value from GPT > 200 IU; HBsAg(−) serum C

DETAILED DESCRIPTION OF THE INVENTION

Each abbreviation of amino acid residues used in this specification means the following respectively:

| Ala: | L-alanine residue | Arg: | L-arginine residue |
|---|---|---|---|
| Asn: | L-asparagine residue | Asp: | L-aspartic acid residue |
| Cys: | L-cysteine residue | Gln: | L-glutamine residue |
| Glu: | L-glutamic acid residue | Gly: | glycine residue |
| His: | L-histidine residue | Ile: | L-isoleucine residue |
| Leu: | L-leucine residue | Lys: | L-lysine residue |
| Met: | L-methionine residue | Phe: | L-phenylalanine residue |
| Pro: | L-proline residue | Ser: | L-serine residue |
| Thr: | L-threonine residue | Trp: | L-tryptophan residue |
| Tyr: | L-tyrosine residue | Val: | L-valine residue |

In the present specification, amino acid sequences are described so that the N-terminal amino acid residue is located on the left and the C-terminal amino acid residue is located on the right in accordance with the common practice.

The peptide of the present invention is capable of specifically binding to an antibody specific to HCV-associated antigen, having at least the amino acid sequence:

| Lys Arg Ser Thr Asn, | (SEQ ID NO: 2) |
| Arg Arg Tyr Lys Glu Lys Glu Lys, or | (SEQ ID NO: 4) |
| Ala Ile Ile Pro Asp Arg Glu Val Leu Tyr. | (SEQ ID NO: 6) |

Of these partial amino acid sequences, Lys Arg Ser Thr Asn (SEQ ID NO: 2) offers particularly high antigenicity for the peptide, and this peptide can preferably be used for assay of antibodies specific to HCV-associated antigen.

There is no limitation on the peptide of the present invention, as long as it has the partial amino acid sequence described above, but it is normally a peptide comprising 10 to 40 amino acids.

Specifically, examples of the peptide of the present invention include the following peptide and peptides comprising its fragment.

Accordingly, the peptide of the present invention is the peptide having the amino acid sequence represented by the formula (I) above or a peptide having its fragment, which peptide has the amino acid sequence Lys Arg Ser Thr Asn (SEQ ID No: 2) and which peptide is capable of specifically binding to an antibody specific to HCV-associated antigen. Here, the peptide comprising said fragment is exemplified by the following fragment peptide (I-a), but this is not to be construed as limitative.

formula (I-a):
Thr Lys Arg Ser Thr Asn Arg Arg Arg Ser  (SEQ ID NO: 7)

The peptide of the present invention is the peptide having the amino acid sequence represented by the formula (II) above or a peptide having its fragment, which peptide has the amino acid sequence Arg Arg Tyr Lys Glu Lys Glu Lys (SEQ ID NO: 4) and which peptide is capable of specifically binding to an antibody specific to HCV-associated antigen. Here, the peptide comprising said fragment is exemplified by the following fragment peptide (II-a), (II-b) and (II-c) but these are not to be construed as limitative.

formula (II-a):
Arg Arg Tyr Lys Glu Lys Glu Lys Thr Ala (SEQ ID NO: 8)
Asn Pro Gly Lys Asn Lys Lys Pro Arg formula (II-b):
Thr His Lys Lys Gln Arg Arg Tyr Lys     (SEQ ID NO: 9)
Glu Lys Glu Lys formula (II-c):
Arg Arg Tyr Lys Glu Lys Glu Lys Thr     (SEQ ID NO: 10)
Ala The peptide of the present invention is the peptide having the amino acid sequence represented by the formula (III) above or a peptide having its fragment, which peptide has the amino acid sequence Ala Ile Ile Pro Asp Arg Glu Val Leu Tyr (SEQ ID NO: 6) and which peptide is capable of specifically binding to an antibody specific to HCV-associated antigen. Here, the peptide comprising said fragment is exemplified by the following fragment peptide (III-a), (III-b) and (III-c) but these are not to be construed as limitative.

formula (III-a):
Ala Ile Ile Pro Asp Arg Glu Val Leu Tyr Arg Glu
Phe Asp Glu Met Glu Glu Cys Ser Gln His Leu Pro
Tyr Ile Glu Gln Gly Met Met (SEQ ID NO: 11)

formula (III-b):
Arg Val Val Leu Ser Gly Lys Pro Ala Ile Ile Pro
Asp Arg Glu Val Leu Tyr (SEQ ID NO: 12)

formula (III-c):
Ala Ile Ile Pro Asp Arg Glu Val Leu Tyr
(SEQ ID NO: 13)

The peptide of the present invention is exemplified by various peptides as above, but preference is given to the peptide of formula (I-a) from the viewpoint of reaction specificity.

The peptide of the present invention is capable of specifically binding to an antibody specific to such an HCV antigen.

The peptide of the present invention can be synthesized by an ordinary method of peptide synthesis such as the solid phase synthesis method or a liquid phase synthesis method such as the stepwise elongation method or the fragment condensation method, but the solid phase synthesis method is preferred since it is simple to operate [Journal of the American Chemical Society, vol. 85, pp. 2149-2154 (1963); Seikagaku Jikken Koza 1: Tanpakushitsu no Kagaku IV, Kagaku Shusyoku to Pepuchido Gosei, edited by the Japanese Biochemical Society, published by Tokyo Kagaku Dojin, Nov. 15, 1977, pp. 207-495; Zoku Seikagaku Jikken Koza 2: Tanpakushitsu no Kagaku (II), edited by the Japanese Biochemical Society, published by Tokyo Kagaku Dojin, May 20, 1987, pp. 641-694].

Production of the peptide of the present invention by the solid phase synthesis method is carried out, for example, by repeating the process of binding an amino acid corresponding to the C-terminal of the desired peptide or the amide thereof to a polymer insoluble in reaction solvent such as styrene-divinylbenzene copolymer via the α—COO— group or α—CONH— group obtained by eliminating the hydrogen atom from the α—COOH group or α—CONH$_2$ group contained therein and subsequently condensing and binding the corresponding amino acid or peptide fragment to the amino acid or its amide in the direction of the N-terminal of the desired peptide after protecting the functional group other than the α—COOH group contained in the amino acid or peptide fragment such as α-amino acid and the process of eliminating the protective group bound to the amino group which forms the peptide linkage, such as α-amino group, in the bound amino acid or peptide fragment to elongate the peptide chain to a peptide chain corresponding to the desired peptide, then eliminating the peptide chain from the polymer and removing the protective group from the protected functional group to yield the desired peptide, which is then purified. Here, it is preferable from the viewpoint of suppression of side reaction that the elimination of the peptide chain from the polymer and the removal of the protective group be conducted simultaneously using hydrogen fluoride. Also, it is efficient to purify the obtained peptide by reversed phase liquid chromatography.

Since the peptide of the present invention is capable of specifically binding to anti-HCV antibody, it serves well as an assay reagent for the detection of the anti-HCV antibody which appears due to HCV infection.

Accordingly, the assay reagent of the present invention comprises the peptide of the present invention; the peptide of the present invention is used singly or in combination of two or more kinds.

Anti-HCV antibody assay using the peptide of the present invention is carried out on the basis of any one of fluorescent immunoassay, passive hemagglutination, radioimmunoassay and enzyme immunoassay, which are all known methods. The assay procedure based on enzyme immunoassay, for instance, is described below.

The entire assay system comprises a carrier, the peptide of the present invention as the assay reagent, a blocking agent, a subject sample, a labeled antibody, an enzyme, and a coloring agent. The carrier is coated with the peptide of the present invention and then reacted with the blocking agent to block the nonspecific protein binding site on the carrier. The subject sample is added to the peptide-coated carrier, followed by incubation. Subsequently, the enzyme-labeled antibody is brought into contact with the carrier, followed by incubation. The coloring agent is then added to the carrier thus treated, followed by incubation. The amount of reaction product produced in the reaction between the enzyme and the coloring agent is determined using a spectrometer. The peptide of the present invention may be used singly or in combination of two or more kinds for coating. It is preferable to use an enzyme immunoassay cup or beads of glass or resin as the carrier. Prior to assay runs, the peptide of the present invention is dissolved in a 0.01M carbonate buffer. The resulting solution is added to, for example, a polystyrene enzyme immunoassay cup and then kept standing at 4° C. overnight or at room temperature for 3 hours, whereby the surface of the carrier is coated with the peptide of the present invention. Examples of the blocking agent to block the nonspecific protein binding site on the carrier include bovine serum albumin, casein, powdered skim milk, serum of immunogen animals for antihuman IgG antibody or antihuman IgM antibody, and gelatin. Examples of the labeling antibody include antihuman IgG antibody and antihuman IgM antibody. Examples of the enzyme include alkaline phosphatase, glucose oxidase, peroxidase and beta galactosidase. It is preferable to prepare a conjugate as a part of the entire assay system by binding the enzyme to the labeling antibody using a compound having two or more functional groups, such as glutaraldehyde, before assay runs. An appropriate coloring agent is selected according to the selected enzyme. For example, when selecting peroxidase as the enzyme, o-phenylenediamine is preferred.

As stated above, the present invention provides a peptide capable of specifically binding to anti-HCV antibody. This peptide makes it possible to provide an assay reagent for anti-HCV antibody which is more sensitive and more specific than the conventional assay reagents for anti-HCV antibody.

EXAMPLES

The present invention is hereinafter described in more detail by means of the following examples, but these are not to be construed as limitative on the present invention.

EXAMPLE 1

The peptide represented by the formula (I):

Lys Asp Arg Thr Gln Gln Arg Lys Thr Lys Arg Ser Thr Asn Arg Arg Arg Ser Lys Asn Glu Lys Lys Lys Lys
(SEQ ID NO: 1)

was synthesized by the solid phase synthesis method using an automatic peptide synthesizer [model 431A, product of Applied Biosystems Inc., USA].

Specifically, 760 mg of a granular resin [PAM Lysine, t-Boc-L-Lys (Cl-Z), product of Applied Biosystems Inc., USA] comprising a styrene-divinylbenzene copolymer [styrene-divinylbenzene molar ratio=99:1] containing 4-[$N^\alpha$-(t-butoxycarbonyl)-$N^\epsilon$-(2-chlorobenzyloxycarbonyl)-L-lysyloxymethyl]-phenylacetylamidomethyl group

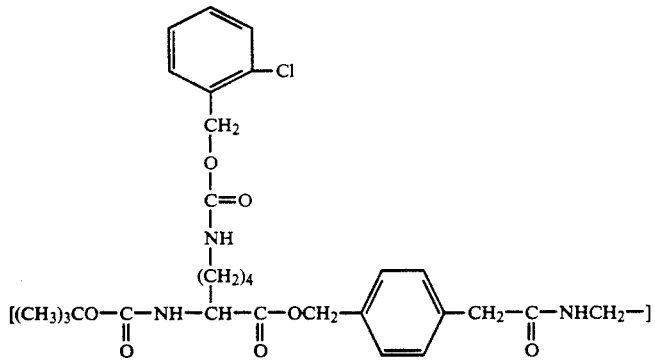

in a ratio of 0.65 mmol/g (resin) was sequentially bound with the corresponding L-arginine, L-asparagine, L-aspartic acid, L-glutamine, L-glutamic acid, L-lysine, L-serine, and L-threonine in this order in the direction of the N-terminal of the desired peptide in accordance with the series of procedures shown in table 1. In the condensation reaction, the above-mentioned amino acids were used as $N^\alpha$-(t-butoxycarbonyl)-$N^\gamma$-(mesitylene-2-sulfonyl)-L-arginine, N-(t-butoxycarbonyl)-L-asparagine, N-(t-butoxycarbonyl)-L-aspartic acid-$\beta$-benzyl ester, N-(t-butoxycarbonyl)-L-glutamine, N-(t-butoxycarbonyl)-L-glutamic acid-$\gamma$-benzyl ester, $N^\alpha$-(t-butoxycarbonyl)-$N^\epsilon$-(2-chlorobenzyloxycarbonyl)-L-lysine, N-(t-butoxycarbonyl)-O-benzyl-L-serine, and N-(t-butoxycarbonyl)-O-benzyl-L-threonine, respectively, and the molar amount of their use was about 4 times the amount of the substrate. Condensation reaction was carried out at room temperature. The reaction time for the entire process needed to bind one amino acid residue ranged from 100 to 110 minutes. After completion of the reaction procedure for all amino acids, the resulting resin was washed by sequential addition of dichloromethane and methanol on a glass filter and then vacuum dried to yield 2.58 g of the dry resin. Then, 0.7 g of the obtained resin was mixed with 1.05 ml of anisole and 0.175 ml of ethyl methyl sulfide in a polytrifluoromonochloroethylene reaction vessel (HF-reactor I type, product of Peptide Institute, Inc.). To this mixture 7.0 ml of hydrogen fluoride was added at a temperature of $-20°$ C., followed by stirring at that temperature for 30 minutes and then at 0° C. for 30 minutes. From the resulting reaction mixture, the hydrogen fluoride, anisole and ethyl methyl sulfide were evaporated off under reduced pressure, and the resulting residue was thoroughly washed with diethyl ether and dichloromethane on a glass filter. The washed residue was extracted with 2N aqueous acetic acid, and the extract was lyophilized to yield 200 mg of a crude peptide. The crude product thus obtained was subjected to preparative reversed phase high performance liquid chromatography [column: packed with octadecylated silica gel (15 $\mu$m in grain diameter), inside diameter 50 mm, length 300 mm, product of Waters, division of MILLIPORE, $\mu$ BONDASPHERE 15$\mu$ C18-100; mobile phase: acetonitrile-water mixed solvent containing 0.05% by volume of trifluoroacetic acid (the acetonitrile density was gradually changed from 10% by volume to 20% by volume over a period of 30 minutes); flow rate: 5 ml/min; detection method: spectrophotometry at a wavelength of 210 nm], whereby 80 mg of a purified product of the desired peptide was obtained. The obtained purified product was subjected to analytical reversed phase high performance liquid chromatography [column: packed with octadecylated silica gel (5 $\mu$m in grain diameter), inside diameter 4 mm, length 150 mm, TSK-gel ODS-80TM, product of Tosoh Corporation; mobile phase: acetonitrile-water mixed solvent containing 0.05% by volume of trifluoroacetic acid (the acetonitrile density was gradually changed from 5% by volume to 50% by volume over a period of 30 minutes); flow rate: 1 ml/min; detection method: spectrophotometry at a wavelength of 210 nm]; a single acute peak appeared at a retention time of 15.0 minutes. The molecular weight of the purified product was determined to be 3188 by fast atomic bombardment (hereinafter abbreviated FAB) mass spectrometry (theoretical value=3187.53).

TABLE 1

| Process | Solvent and/or reagent used | Time (min) | Frequency |
|---|---|---|---|
| 1: t-butoxy-carbonyl group removal | Trifluoroacetic acid | 20 | 1 |
| 2: Washing | Dichloromethane | 3 | 1 |
| 3: Neutralization | N-methylpyrrolidone solution containing 5% diisopropylethylamine | 4 | 1 |
| 4: Washing | N-methylpyrrolidone | 5 | 1 |
| 5: Condensation | N-methylpyrrolidone solution containing amino acid, dimethylsulfoxide and diisopropylethylamine | 55 | 1 |
| 6: Washing | N-methylpyrrolidone | 5 | 1 |
| 7: Unreacted amine inactivation | 10% acetic anhydride and N-methylpyrrolidone solution containing 5% diisopropylethylamine | 9 | 1 |
| 8: Washing | Dichloromethane | 4 | 1 |

Example 2

The peptide represented by the formula (I-a): Thr Lys Arg Ser Thr Asn Arg Arg Arg Ser (SEQ ID NO: 7) was obtained by solid phase synthesis and purification of peptide in the same manner as in Example 1. The obtained peptide was subjected to analytical reversed phase high performance liquid chromatography [conditions were the same as above]; a single acute peak appeared at a retention time of 14.2 minutes. The molecular weight of the peptide was determined to be 1243 by FAB mass spectrometry (theoretical value=1243.33).

Example 3

The peptide represented by the formula (II-a): Arg Arg Tyr Lys Glu Lys Glu Lys Thr Ala Thr Asn Asn Pro Gly Lys Asn Lys Lys Pro Arg (SEQ ID NO: 8) was obtained by solid phase synthesis and purification of peptide in the same manner as in Example 1. The obtained peptide was subjected to analytical reversed phase high performance liquid chromatography [conditions were the same as above]; a single acute peak appeared at a retention time of 22.0 minutes. The molecular weight of the peptide was determined to be 2542 by FAB mass spectrometry (theoretical value=2541.85).

Example 4

The peptide represented by the formula (II-b): Thr His Lys Lys Gln Arg Arg Tyr Lys Glu Lys Glu Lys (SEQ ID NO: 9) was obtained by solid phase synthesis and purification of peptide in the same manner as in Example 1. The obtained peptide was subjected to analytical reversed phase high performance liquid chromatography [conditions were the same as above]; a single acute peak appeared at a retention time of 14.3 minutes. The molecular weight of the peptide was determined to be 1758 by FAB mass spectrometry (theoretical value=1758.01).

Example 5

The peptide represented by the formula (II-c): Arg Arg Tyr Lys Glu Lys Glu Lys Thr Ala (SEQ ID NO: 10) was obtained by solid phase synthesis and purification of peptide in the same as in Example 1. The obtained peptide was subjected to analytical reversed phase high performance liquid chromatography [conditions were the same as above]; a single acute peak appeared at a retention time of 14.5 minutes. The molecular weight of the peptide was determined to be 1306 by FAB mass spectrometry (theoretical value=1306.49).

Example 6

The peptide represented by the formula (III-a): Ala Ile Ile Pro Asp Arg Glu Val Leu Tyr Arg Glu Phe Asp Glu Met Glu Glu Cys Ser Gln His Leu Pro Tyr Ile Glu Gln Gly Met Met (SEQ ID NO: 11) was obtained by solid phase synthesis and purification of peptide in the same manner as in Example 1. The obtained peptide was subjected to analytical reversed phase high performance liquid chromatography [conditions were the same as above]; a single acute peak appeared at a retention time of 29.8 minutes. The molecular weight of the peptide was determined to be 3785 by FAB mass spectrometry (theoretical value=3785.19).

Example 7

The peptide represented by the formula (III-b): Arg Val Val Leu Ser Gly Lys Pro Ala Ile Ile Pro Asp Arg Glu Val Leu Tyr (SEQ ID NO: 12) was obtained by solid phase synthesis and purification of peptide in the same manner as in Example 1. The obtained peptide was subjected to analytical reversed phase high performance liquid chromatography [conditions were the same as above]; a single acute peak appeared at a retention time of 28.7 minutes. The molecular weight of the peptide was determined to be 1953 by FAB mass spectrometry (theoretical value=1953.15).

Example 8

The peptide represented by the formula (III-c): Ala Ile Ile Pro Asp Arg Glu Val Leu Tyr (SEQ ID NO: 13) was obtained by solid phase synthesis and purification of peptide in the same manner as in Example 1. The obtained peptide was subjected to analytical reversed phase high performance liquid chromatography [conditions were the same as above]; a single acute peak appeared at a retention time of 26.9 minutes. The molecular weight of the peptide was determined to be 1203 by FAB mass spectrometry (theoretical value=1203.34).

Reference Example 1

Of the peptides having the amino acid sequence represented by the formula (I), the peptide represented by the formula: Lys Asp Arg Thr Gln Gln Arg Lys Thr Lys (SEQ ID NO: 14), which lacks the amino acid sequence represented by the formula: Lys Arg Ser Thr Asn (SEQ ID NO: 2) was obtained by solid phase synthesis and purification of peptide in the same manner as in Example 1. The obtained peptide was subjected to analytical reversed phase high performance liquid chromatography [conditions were the same as above]; a single acute peak appeared at a retention time of 11.9 minutes. The molecular weight of the peptide was determined to be 1290 by FAB mass spectrometry (theoretical value=1290.39).

Reference Example 2

Of the peptides having the amino acid sequence represented by the formula (I), the peptide represented by the formula: Arg Ser Thr Asn Arg Arg Arg Ser Lys Asn Glu Lys Lys Lys Lys (SEQ ID NO: 15), which lacks the amino acid sequence represented by the formula: Lys Arg Ser Thr Asn (SEQ ID NO: 2) was obtained by solid phase synthesis and purification of peptide in the same manner as in Example 1. The obtained peptide was subjected to analytical reversed phase high performance liquid chromatography [conditions were the same as above]; a single acute peak appeared at a retention time of 13.6 minutes. The molecular weight of the peptide was determined to be 1915 by FAB mass spectrometry (theoretical value = 1915.16).

Reference Example 3

The peptide represented by the formula: Glu Gln Asp Gln Ile Lys Thr Lys Asp Arg Thr Gln Gln Arg Lys Thr Lys Arg Ser Thr Asn Arg Arg Arg Ser Lys Asn Glu Lys Lys Lys Lys (SEQ ID NO: 16) was obtained by solid phase synthesis and purification of peptide in the same manner as in Example 1. The obtained peptide was subjected to analytical reversed phase high performance liquid chromatography [conditions were the same as above]; a single acute peak appeared at a retention time of 24.6 minutes. The molecular weight of the peptide was determined to be 4031 by FAB mass spectrometry (theoretical value = 4031.38).

Reference Example 4

Of the peptides having the amino acid sequence represented by the formula (II), the peptide represented by the formula: Glu Lys Lys Gly Glu Ala Ser Asn Gly Glu Ala Glu Asn Asp (SEQ ID NO: 17), which lacks the amino acid sequence represented by the formula: Arg Arg Tyr Lys Glu Lys Glu Lys (SEQ ID NO: 4) was obtained by solid phase synthesis and purification of peptide in the same manner as in Example 1. The obtained peptide was subjected to analytical reversed phase high performance liquid chromatography [conditions were the same as above]; a single acute peak appeared at a retention time of 14.9 minutes. The molecular weight of the peptide was determined to be 1473 by FAB mass spectrometry (theoretical value = 1473.47).

Reference Example 5

Of the peptides having the amino acid sequence represented by the formula (II), the peptide represented by the formula: Thr Asn Asn Pro Gly Lys Asn Lys Lys Pro Arg (SEQ ID NO: 18), which lacks the amino acid sequence represented by the formula: Arg Arg Tyr Lys Glu Lys Glu Lys (SEQ ID NO: 4) was obtained by solid phase synthesis and purification of peptide in the same manner as in Example 1. The obtained peptide was subjected to analytical reversed phase high performance liquid chromatography [conditions were the same as above]; a single acute peak appeared at a retention time of 12.6 minutes. The molecular weight of the peptide was determined to be 1253 by FAB mass spectrometry (theoretical value = 1253.38).

Reference Example 6

Of the peptides having the amino acid sequence represented by the formula (II), the peptide represented by the formula: Val Gly Arg Ile Lys Asn Trp Asn Arg Glu Gly Arg Lys Asp Ala Tyr Gln Ile Arg Lys Arg (SEQ ID NO: 19), which lacks the amino acid sequence represented by the formula: Arg Arg Tyr Lys Glu Lys Glu Lys (SEQ ID NO: 4) was obtained by solid phase synthesis and purification of peptide in the same manner as in Example 1. The obtained peptide was subjected to analytical reversed phase high performance liquid chromatography [conditions were the same as above]; a single acute peak appeared at a retention time of 19.4 minutes. The molecular weight of the peptide was determined to be 2644 by FAB mass spectrometry (theoretical value = 2643.92).

Reference Example 7

Of the peptides having the amino acid sequence represented by the formula (III), the peptide represented by the formula: Arg Val Val Leu Ser Gly Lys Pro Ala Ile Ile (SEQ ID NO: 20), which lacks the amino acid sequence represented by the formula: Ala Ile Ile Pro Asp Arg Glu Val Leu Tyr (SEQ ID NO: 6) was obtained by solid phase synthesis and purification of peptide in the same manner as in Example 1. The obtained peptide was subjected to analytical reversed phase high performance liquid chromatography [conditions were the same as above]; a single acute peak appeared at a retention time of 26.7 minutes. The molecular weight of the peptide was determined to be 1081 by FAB mass spectrometry (theoretical value = 1081.20).

Reference Example 8

Subject samples
GPT>200 IU; HBsHg(−) serum: 65 specimens
Normal human serum: 10 specimens
Determination by enzyme immunoassay Each serum specimen was examined for anti-HCV antibody by the following enzyme immunoassay procedure.

To 100 μl of a solution containing the phage λ gt11 having #8 clone, #14 clone and #18 clone, all of which were cloned from the ribonucleic acid isolated by several researchers including one of the present inventors, Escherichia coli Y1090, as the host cell, was added, followed by incubation at 37° C. for 15 minutes, whereby the phage was infected to the E. coli bacterium. Subsequently, the mixture described above was inoculated to an agar medium containing 50 μg/ml ampicillin and cultivated at 43° C. for 3 hours. Next, a nitrocellulose film, immersed in a 10 mM aqueous solution of IPTG for 2 hours and the air dried, was placed on the agar medium described above, followed by incubation at 37° C. for 3 hours. The nitrocellulose film thus treated was washed with three portions of 10 mM tris-HCl (pH 7.5) containing 150 mM NaCl (hereinafter referred to as TS Buffer), and then shaken in 20 mM tris-HCl (pH 7.5) containing 500 mM NaCl and 3% gelatin at room temperature overnight to block the nonspecific protein binding site on the film. Subsequently, the film was washed by shaking in TS Buffer for 2 minutes. The nitrocellulose film obtained above was immersed in a solution obtained by diluting the serum specimen with TS Buffer containing 1% gelatin and then shaken at room temperature for 3 hours. The nitrocellulose film thus treated was shaken in TS Buffer containing 0.05% Tween 20 (hereinafter referred to as TS-T Buffer) at room temperature for 5 minutes. This procedure was repeated in five cycles. Subsequently, the nitrocellulose film was immersed in a goat antihuman IgG antibody-peroxidase conjugate (diluted to an optimum concentration with TS Buffer containing 1% gelatin) and shaken at room temperature for 1.5 hours. The nitrocellulose film thus treated was shaken in TS-T Buffer at room temperature for 5 minutes. This procedure was repeated in five cycles.

Next, the nitrocellulose film was shaken in TS Buffer containing 0.05% HRP-color (product of Bio-Rad Laboratories), 0.05% H$_2$O$_2$ and 17% methanol for a coloring reaction, after which it was shaken in distilled water at room temperature for 5 minutes. This procedure was repeated in five cycles. After air drying, it was judged whether the serum contained anti-HCV antibody or not on the basis of the presence or absence of coloring.

Further, nucleotide sequence of #8 clone (SEQ ID NO: 21) denotes the following:

```
GAATTCCAAA  AAGAGCAAAA  CAAACCGCCG  AAGAAAAAAC  TAATAAGAGA   50
AGAAAAGGCG  AAGAGACACA  GGAAAAAAAA  AACAGAGACG  AAGGTCAGAT  100
AGAAAAAAAG  CAAGGAATTC                                      120
```

Nucleotide sequence of #14 clone (SEQ ID NO: 22) denotes the following:

```
GAATTCCGAG  AACAAGACCA  GATAAAAACC  AAAGACAGAA  CACAACAGAG   50
AAAGACGAAA  AGAAGCACCA  ATCGCAGGCG  AAGCAAAAAC  GAAAAAAAAA  100
AAAAAAAGGA  ATTC                                            114
```

Nucleotide sequence of #18 clone (SEQ ID NO: 23) denotes the following:

```
GAATTCCAAG  AAAAAAAGGG  AGAAGCCAGC  AATGGAGAAG  CCGAAAACGA   50
CACACACAAG  AAACAAAGGA  GGTACAAAGA  AAAAGAAAAA  ACGGCAACAA  100
ATAACCCAGG  AAAGAACAAA  AAGCCAAGAG  TGGGCAGAAT  AAAAAACTGG  150
AACCGGGAGG  GAAGGAAGGA  CGCATATCAG  ATTAGAAAAA  GGAGGGAATT  200
C                                                           201
```

Results

Assay results are given in Table 2, showing that the 65 specimens of GPT>200 IU; HBsHg(−) serum can be classified into three groups, namely the group A, found to be positive for two clones of #14 clone and #18 clone, the group B, found to be positive for three clones of #8 clone, #14 clone and #18 clone, and the group C, found to be negative for all of #8 clone, #14 clone and #18 clone.

TABLE 2

| GPT > 200 IU; HBsAg(−) serum | Number of specimens |
| --- | --- |
| #8(−), #14(+), #18(+) | 30 |
| #8(+), #14(+), #18(+) | 15 |
| #8(−), #14(−), #18(−) | 20 |
| Total number | 65 |

| Normal human serum | Number of specimens |
| --- | --- |
| #8(−), #14(−), #18(−) | 10 |
| Total number | 10 |

Example 9

Subject samples

The sera classified in Reference Example 8 were used.
GPT>200 IU; HBsAg(−) serum A: 30 specimens
GPT>200 IU; HBsAg(−) serum B: 15 specimens
GPT>200 IU; HBsAg(−) serum C: 20 specimens
Normal human serum D: 10 specimens Determination by enzyme immunoassay Each serum specimen was examined for anti-HCV antibody by determining the absorbance by the following enzyme immunoassay procedure.

Each of the peptides obtained in Examples 1 and 2 and Reference Examples 1, 2 and 3, as the antigen, was dissolved in 0.01M carbonate buffer (pH 9.5). Each obtained peptide solution was added to a polystyrene enzyme immunoassay cup (product of Dynatech Laboratories Incorporation) at 100 μl per cup and kept standing at 4° C. for 12 hours for peptide coating. After removing the peptide solution from each assay cup, 150 μl of 0.01M phosphate buffered saline (hereinafter abbreviated PBS) containing 20% by volume of normal goat serum was added, and each cup was kept standing at room temperature for 3 hours to block the nonspecific protein binding site. Then, after removing the PBS containing 20% by volume of normal goat serum used for blocking, each assay cup was dried.

To each assay cup described above, 100 μl of PBS containing 10% by volume of normal goat serum, as the serum diluent, was added, whereafter each subject serum (30 specimens of GPT>200 IU; HBsAg(−) serum A, 15 specimens of GPT>200 IU; HBsAg(−) serum B, 20 specimens of GPT>200 IU; HBsAg(−) serum C, and 10 specimens of normal human serum D) was added so that the ratio of the serum diluent to the subject serum became 20 to 1 (by volume). After incubation at 37° C. for 1 hour, each cup was washed with three portions of PBS containing 0.05% by volume of Tween 20.

To each assay cup thus treated, 100 μl of a goat anti-human IgG antibody-peroxidase conjugate (diluted to an optimum concentration with PBS containing 10% by volume of normal goat serum) was added. After incubation at 37° C. for 30 minutes, each cup was washed with three portions of PBS containing 0.5% by volume of Tween 20. Subsequently, to each assay cup thus treated, 100μl of coloring agent (prepared by dissolving o-phenylenediamine in a 0.1M citrate-phosphate buffer, pH 5.6, containing 0.02% by volume of hydrogen peroxide, to a final concentration of 0.3% by weight) was added. After this mixture was kept standing at room temperature for 15 minutes, 100 μl of 2N sulfuric acid was added to stop the reaction, and the absorbance $OD_{492}$ at 492 nm of the reaction mixture was determined.

Results

Assay results obtained are given in Tables 3, 4, 5 and 6, respectively for serum A, Serum B, serum C and serum D assayed by enzyme immunoassay using the peptides obtained in Examples 1 and 2 and Reference Examples 1 through 3. Also, a cut-off value was set from the $OD_{492}$ value of 10 specimens of normal human serum D, based on which the response to anti-HCV antibody was judged to be positive or negative. The cut-off value was calculated using the equation:

Cut-off value=mean $OD_{492}$ value of normal human serum+2SD

Figure 2:
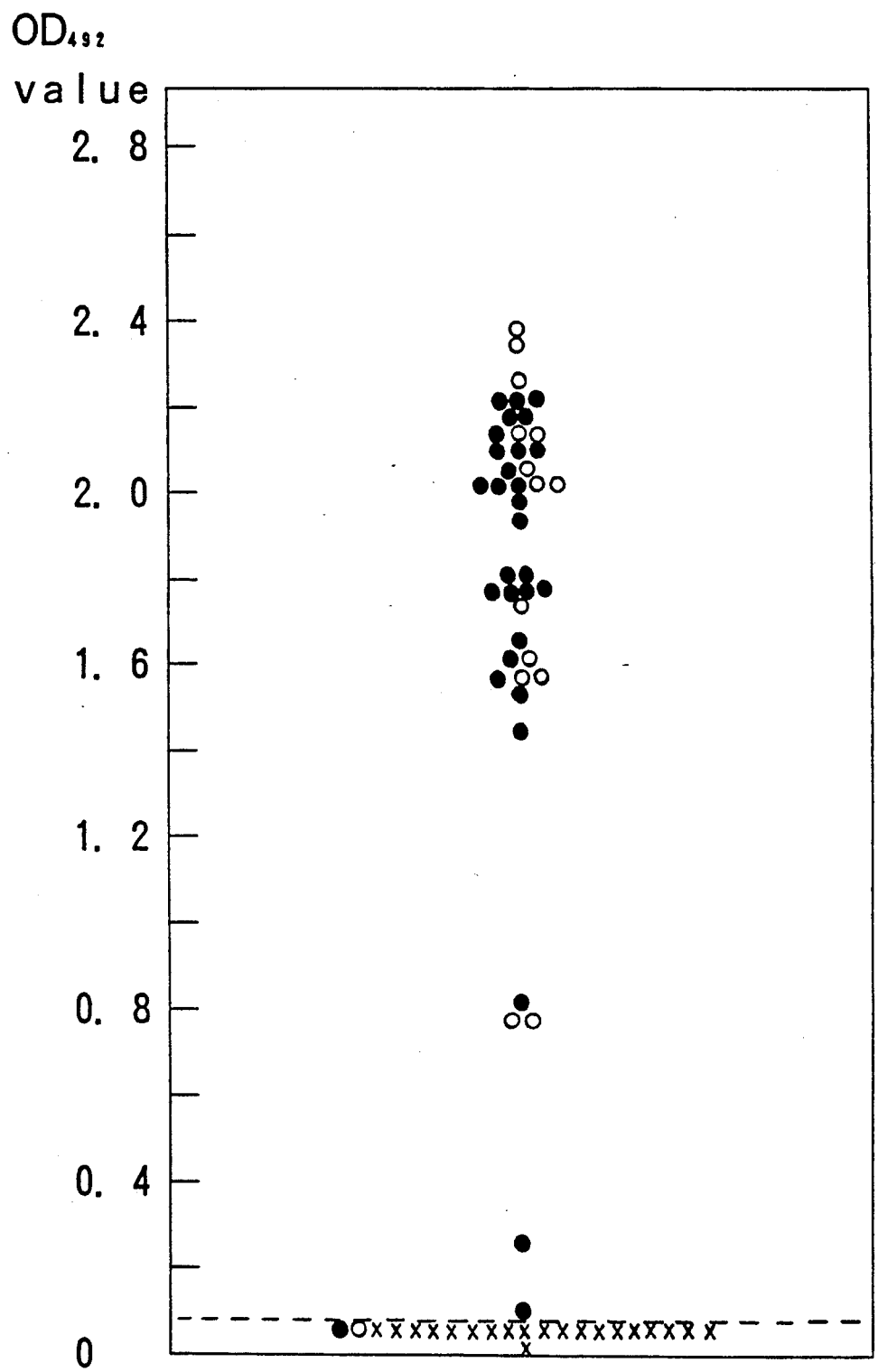
Figure 3:
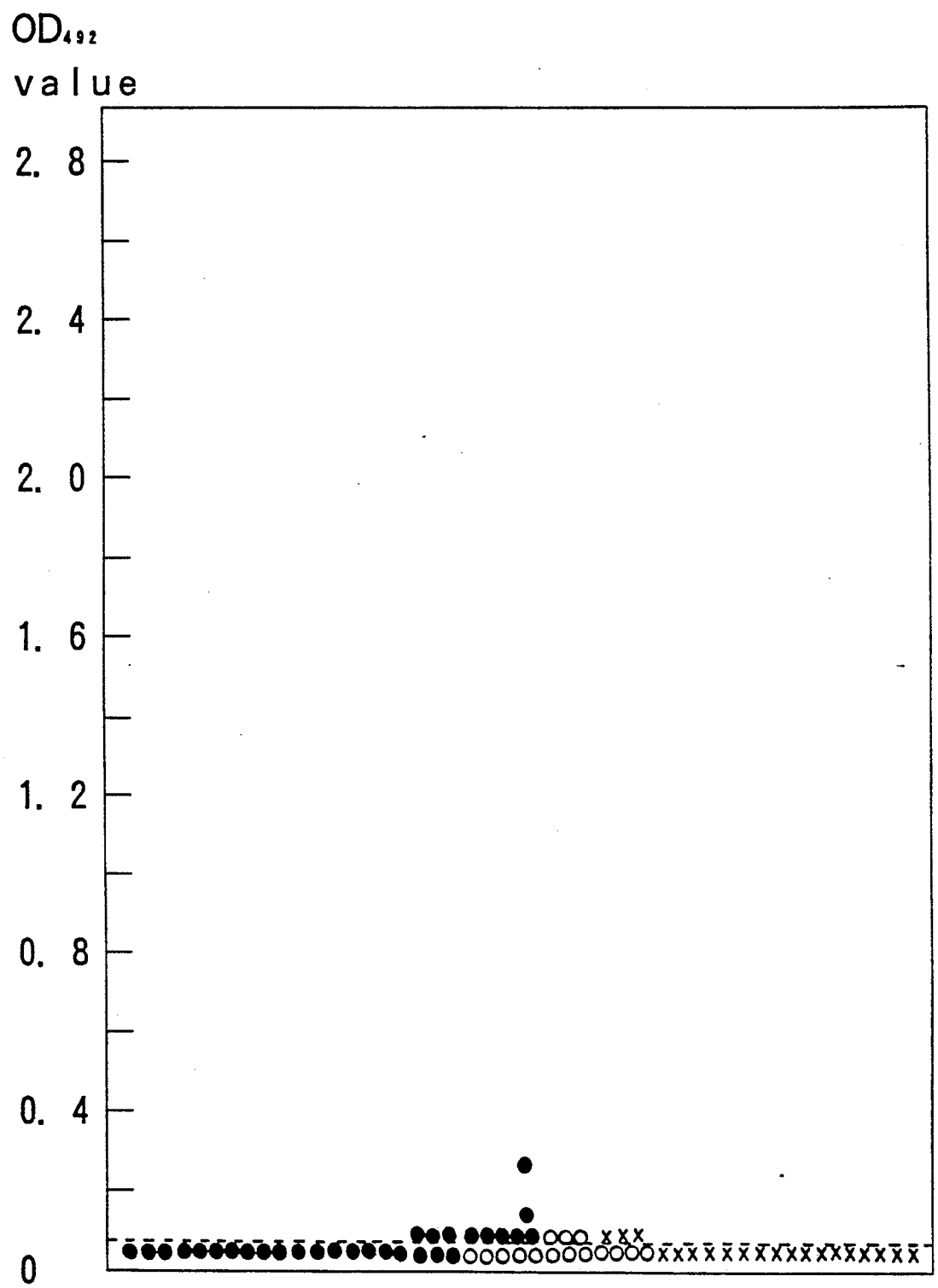
Figure 4:
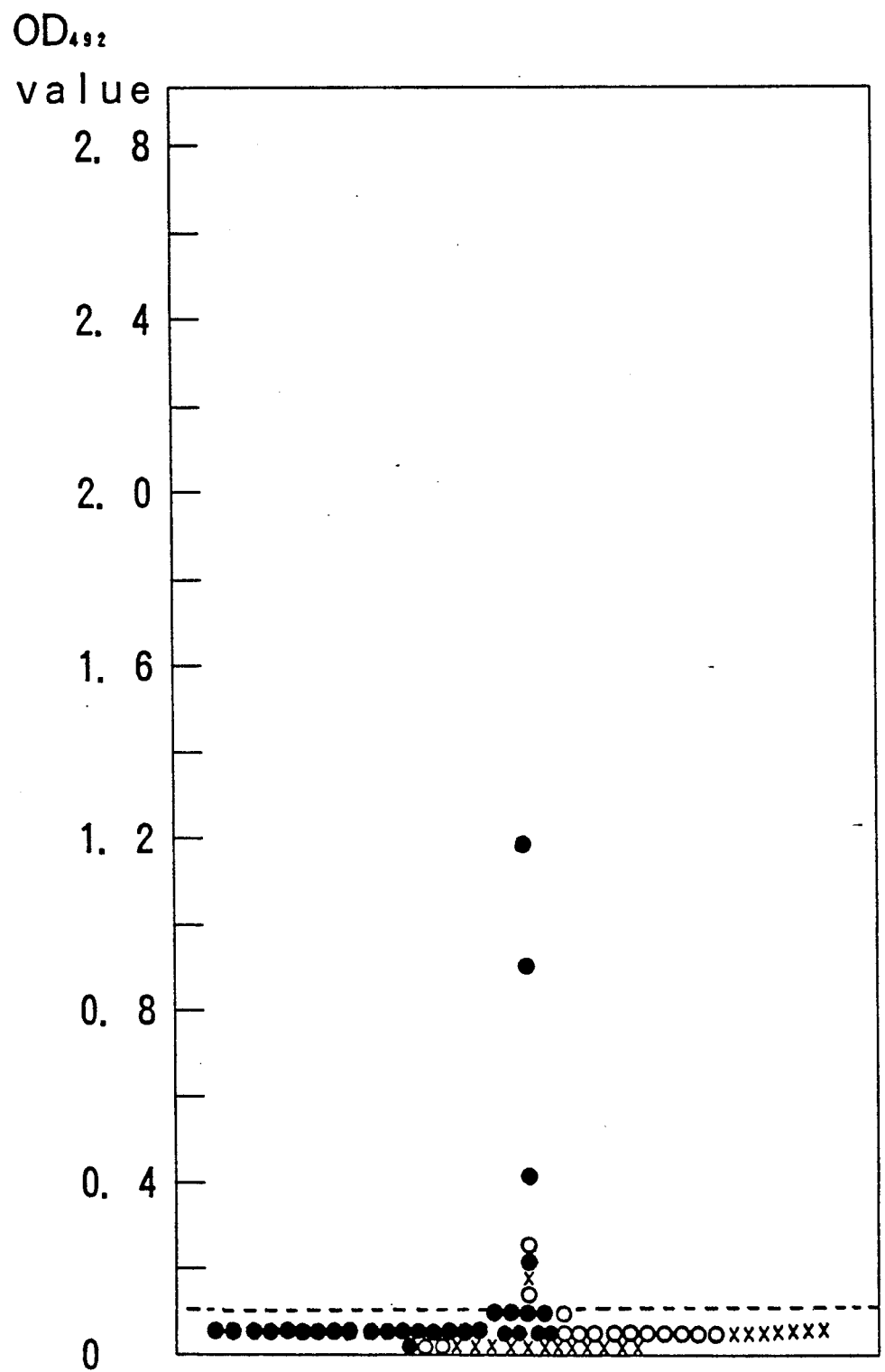
Figure 5:
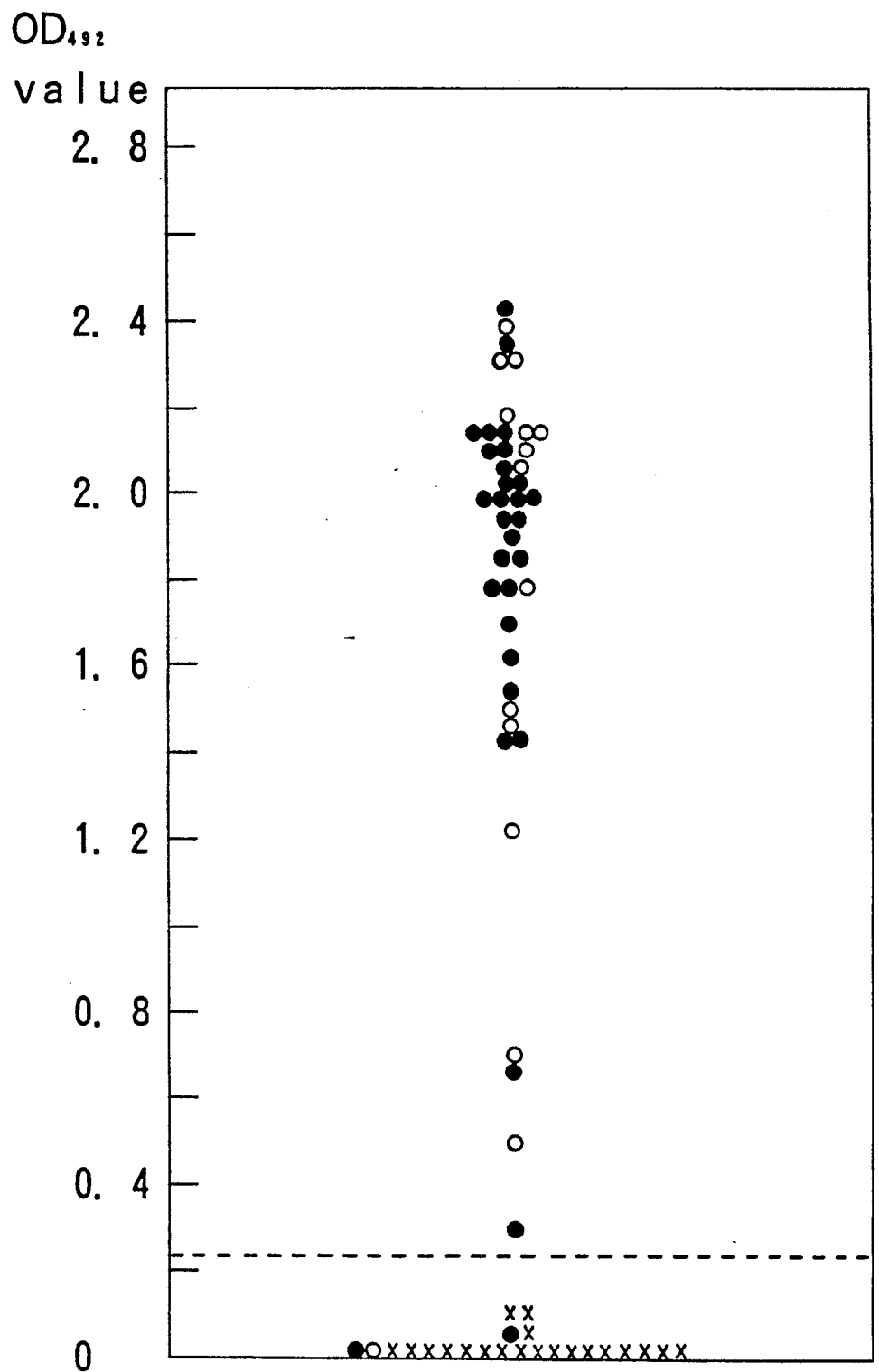

FIGS. 1–5 show the $OD_{492}$ value distributions of the peptides of Examples 1 and 2 and Reference Examples 1 through 3 obtained on the basis of the cut-off value calculated from Tables 3, 4, 5 and 6. In these figures, the symbol  denotes the $OD_{492}$ value from serum A; the symbol ◯ denotes the $OD_{492}$ value from serum B; the symbol × denotes the $OD_{492}$ value from serum C. Table 7 gives the positive response ratios calculated from Tables 3, 4, 5 and 6 and the above-mentioned cut-off value, showing that positive response ratios of 93.3%, 93.3%, 10.0%, and 0% were obtained from serum A, serum B, serum C and normal human serum D, respectively in enzyme immunoassay using the peptide obtained in Example 1. When the peptide obtained in Example 2 was used for enzyme immunoassay, serum A, serum B, serum C and serum D showed positive response ratios of 96.7%, 93.3%, 0.0%, and 0%, respectively. The enzyme immunoassay using these peptides were found to be closely correlated to the immunoscreening method described in Reference Example 8. When the peptides obtained in Reference Examples 1 and 2 were used for enzyme immunoassay, serum A, serum B, serum C and normal human serum D all showed a positive response ratio of about 10.0%, demonstrating that the enzyme immunoassay using these peptides are poor in sensitivity and specificity. When the peptide obtained in Reference Example 3, a peptide comprising the entire amino acid sequence of the peptide translated from one clone selected from the clones isolated and cloned by several researchers including one of the present inventors was used for enzyme immunoassay, serum A, serum B and serum C showed positive response ratios of 93.3%, 93.3% and 0%, respectively, while normal human serum D showed a positive response ratio of 10.0%; it was thus found that there is a possibility of false positive response. In comparison with the enzyme immunoassay using the peptide obtained in Example 1 or 2, this enzyme immunoassay proved to be lower in specificity and sensitivity. These findings demonstrate that the use of the peptides obtained in Examples 1 and 2 permits efficient judgement for the presence or absence of anti-HCV antibody.

TABLE 3

|   | | Peptide obtained in Exam. 1 | Peptide obtained in Exam. 2 | Peptide obtained in Ref. Exam. 1 | Peptide obtained in Ref. Exam. 2 | Peptide obtained in Ref. Exam. 3 |
|---|---|---|---|---|---|---|
| Serum A | 1 | 1.524 | 1.532 | 0.057 | 0.111 | 1.405 |
|   | 2 | 0.073 | 0.081 | 0.052 | 0.053 | 0.041 |
|   | 3 | 2.193 | 2.211 | 0.072 | 0.046 | 2.402 |
|   | 4 | 2.105 | 2.094 | 0.048 | 0.046 | 2.039 |
|   | 5 | 2.192 | 2.189 | 0.044 | 0.043 | 2.106 |
|   | 6 | 2.215 | 2.216 | 0.044 | 0.042 | 1.977 |
|   | 7 | 2.240 | 2.230 | 0.061 | 0.909 | 2.327 |
|   | 8 | 2.101 | 2.086 | 0.047 | 0.053 | 2.034 |
|   | 9 | 2.024 | 2.022 | 0.046 | 0.052 | 1.940 |
|   | 10 | 1.934 | 1.933 | 0.043 | 0.066 | 1.982 |
|   | 11 | 1.743 | 1.764 | 0.044 | 0.041 | 1.794 |
|   | 12 | 2.000 | 1.995 | 0.043 | 1.170 | 1.991 |
|   | 13 | 2.116 | 2.122 | 0.077 | 0.054 | 2.131 |
|   | 14 | 2.100 | 2.084 | 0.055 | 0.047 | 1.971 |
|   | 15 | 1.559 | 1.456 | 0.077 | 0.067 | 1.527 |
|   | 16 | 1.855 | 1.829 | 0.060 | 0.203 | 1.880 |
|   | 17 | 1.619 | 1.654 | 0.060 | 0.062 | 1.618 |
|   | 18 | 1.730 | 1.627 | 0.093 | 0.084 | 1.702 |
|   | 19 | 0.724 | 0.831 | 0.066 | 0.036 | 0.654 |
|   | 20 | 2.076 | 2.003 | 0.051 | 0.042 | 2.050 |
|   | 21 | 0.056 | 0.055 | 0.039 | 0.043 | 0.025 |
|   | 22 | 1.749 | 1.778 | 0.143 | 0.060 | 1.943 |
|   | 23 | 1.614 | 1.564 | 0.071 | 0.068 | 1.428 |
|   | 24 | 1.813 | 1.826 | 0.060 | 0.080 | 1.781 |
|   | 25 | 2.052 | 2.038 | 0.063 | 0.109 | 2.139 |
|   | 26 | 2.208 | 2.195 | 0.054 | 0.049 | 2.133 |
|   | 27 | 1.876 | 1.792 | 0.253 | 0.063 | 1.873 |
|   | 28 | 1.844 | 1.799 | 0.053 | 0.408 | 1.852 |
|   | 29 | 2.090 | 2.051 | 0.093 | 0.066 | 2.150 |
|   | 30 | 0.382 | 0.255 | 0.060 | 0.057 | 0.286 |

TABLE 4

|   | | Peptide obtained in Exam. 1 | Peptide obtained in Exam. 2 | Peptide obtained in Ref. Exam. 1 | Peptide obtained in Ref. Exam. 2 | Peptide obtained in Ref. Exam. 3 |
|---|---|---|---|---|---|---|
| Serum B | 1 | 2.323 | 2.330 | 0.058 | 0.052 | 2.300 |
|   | 2 | 2.002 | 2.023 | 0.045 | 0.060 | 2.067 |
|   | 3 | 1.587 | 1.593 | 0.047 | 0.046 | 1.493 |
|   | 4 | 2.128 | 2.122 | 0.055 | 0.071 | 2.130 |
|   | 5 | 1.579 | 1.562 | 0.046 | 0.041 | 1.200 |
|   | 6 | 0.852 | 0.797 | 0.063 | 0.058 | 0.682 |
|   | 7 | 2.268 | 2.274 | 0.054 | 0.139 | 2.312 |
|   | 8 | 0.053 | 0.065 | 0.037 | 0.026 | 0.023 |
|   | 9 | 2.089 | 2.010 | 0.055 | 0.241 | 2.157 |
|   | 10 | 1.705 | 1.746 | 0.045 | 0.071 | 1.768 |
|   | 11 | 2.105 | 2.135 | 0.066 | 0.095 | 2.164 |
|   | 12 | 2.033 | 2.043 | 0.058 | 0.056 | 2.092 |
|   | 13 | 0.762 | 0.777 | 0.039 | 0.066 | 0.504 |
|   | 14 | 2.334 | 2.396 | 0.078 | 0.075 | 2.384 |
|   | 15 | 1.630 | 1.621 | 0.047 | 0.029 | 1.445 |

TABLE 5

|   | | Peptide obtained in Exam. 1 | Peptide obtained in Exam. 2 | Peptide obtained in Ref. Exam. 1 | Peptide obtained in Ref. Exam. 2 | Peptide obtained in Ref. Exam. 3 |
|---|---|---|---|---|---|---|
| Serum C | 1 | 0.038 | 0.035 | 0.037 | 0.047 | 0.039 |
|   | 2 | 0.054 | 0.055 | 0.064 | 0.061 | 0.025 |
|   | 3 | 0.053 | 0.053 | 0.046 | 0.016 | 0.019 |
|   | 4 | 0.048 | 0.050 | 0.041 | 0.052 | 0.028 |
|   | 5 | 0.046 | 0.045 | 0.046 | 0.190 | 0.040 |
|   | 6 | 0.043 | 0.044 | 0.034 | 0.025 | 0.011 |
|   | 7 | 0.052 | 0.048 | 0.046 | 0.027 | 0.021 |
|   | 8 | 0.052 | 0.049 | 0.043 | 0.036 | 0.021 |
|   | 9 | 0.043 | 0.050 | 0.036 | 0.043 | 0.025 |
|   | 10 | 0.065 | 0.057 | 0.041 | 0.016 | 0.024 |
|   | 11 | 0.059 | 0.066 | 0.045 | 0.040 | 0.014 |
|   | 12 | 0.048 | 0.046 | 0.033 | 0.032 | 0.017 |
|   | 13 | 0.072 | 0.063 | 0.066 | 0.025 | 0.033 |
|   | 14 | 0.072 | 0.064 | 0.056 | 0.062 | 0.021 |
|   | 15 | 0.058 | 0.055 | 0.052 | 0.029 | 0.016 |
|   | 16 | 0.057 | 0.059 | 0.052 | 0.057 | 0.019 |
|   | 17 | 0.067 | 0.054 | 0.038 | 0.039 | 0.024 |
|   | 18 | 0.099 | 0.075 | 0.063 | 0.027 | 0.111 |
|   | 19 | 0.049 | 0.042 | 0.043 | 0.028 | 0.020 |
|   | 20 | 0.215 | 0.076 | 0.053 | 0.035 | 0.105 |

TABLE 6

|   | | Peptide obtained in Exam. 1 | Peptide obtained in Exam. 2 | Peptide obtained in Ref. Exam. 1 | Peptide obtained in Ref. Exam. 2 | Peptide obtained in Ref. Exam. 3 |
|---|---|---|---|---|---|---|
| Serum C | 1 | 0.039 | 0.029 | 0.051 | 0.057 | 0.024 |
|   | 2 | 0.038 | 0.045 | 0.051 | 0.049 | 0.031 |
|   | 3 | 0.071 | 0.042 | 0.077 | 0.079 | 0.292 |
|   | 4 | 0.057 | 0.043 | 0.059 | 0.060 | 0.035 |
|   | 5 | 0.046 | 0.056 | 0.052 | 0.074 | 0.096 |
|   | 6 | 0.070 | 0.063 | 0.060 | 0.109 | 0.056 |
|   | 7 | 0.072 | 0.072 | 0.049 | 0.058 | 0.060 |
|   | 8 | 0.043 | 0.044 | 0.053 | 0.060 | 0.032 |
|   | 9 | 0.055 | 0.050 | 0.063 | 0.083 | 0.053 |
|   | 10 | 0.044 | 0.065 | 0.045 | 0.064 | 0.081 |
| X |  | 0.054 | 0.051 | 0.056 | 0.069 | 0.176 |
| SD |  | 0.014 | 0.013 | 0.009 | 0.018 | 0.079 |
| X + 2SD |  | 0.082 | 0.077 | 0.074 | 0.105 | 0.234 |

TABLE 7

| Example No. of peptide used | Positive ratio of serum A (%) | Positive ratio of serum B (%) | Positive ratio of serum C (%) | Positive ratio of serum D (%) |
|---|---|---|---|---|
| Example 1 | 93.3 (28/30) | 93.3 (14/15) | 10.0 (2/20) | 0.0 (0/10) |
| Example 2 | 96.7 (29/30) | 93.3 (14/15) | 0.0 (0/20) | 0.0 (0/10) |
| Ref. Exam. 1 | 20.0 (6/30) | 6.7 (1/15) | 0.0 (0/20) | 10.0 (1/10) |
| Ref. Exam. 2 | 20.0 (6/30) | 13.3 (2/15) | 5.0 (1/20) | 10.0 (1/10) |
| Ref. Exam. 3 | 93.3 (28/30) | 93.3 (14/15) | 0.0 (0/20) | 10.0 (1/10) |

Example 10

Using the peptides obtained in Examples 3, 4 and 5 and Reference Examples 4, 5 and 6 as antigens, determination was made by enzyme immunoassay in the same manner as in Example 9.

Figure 6:
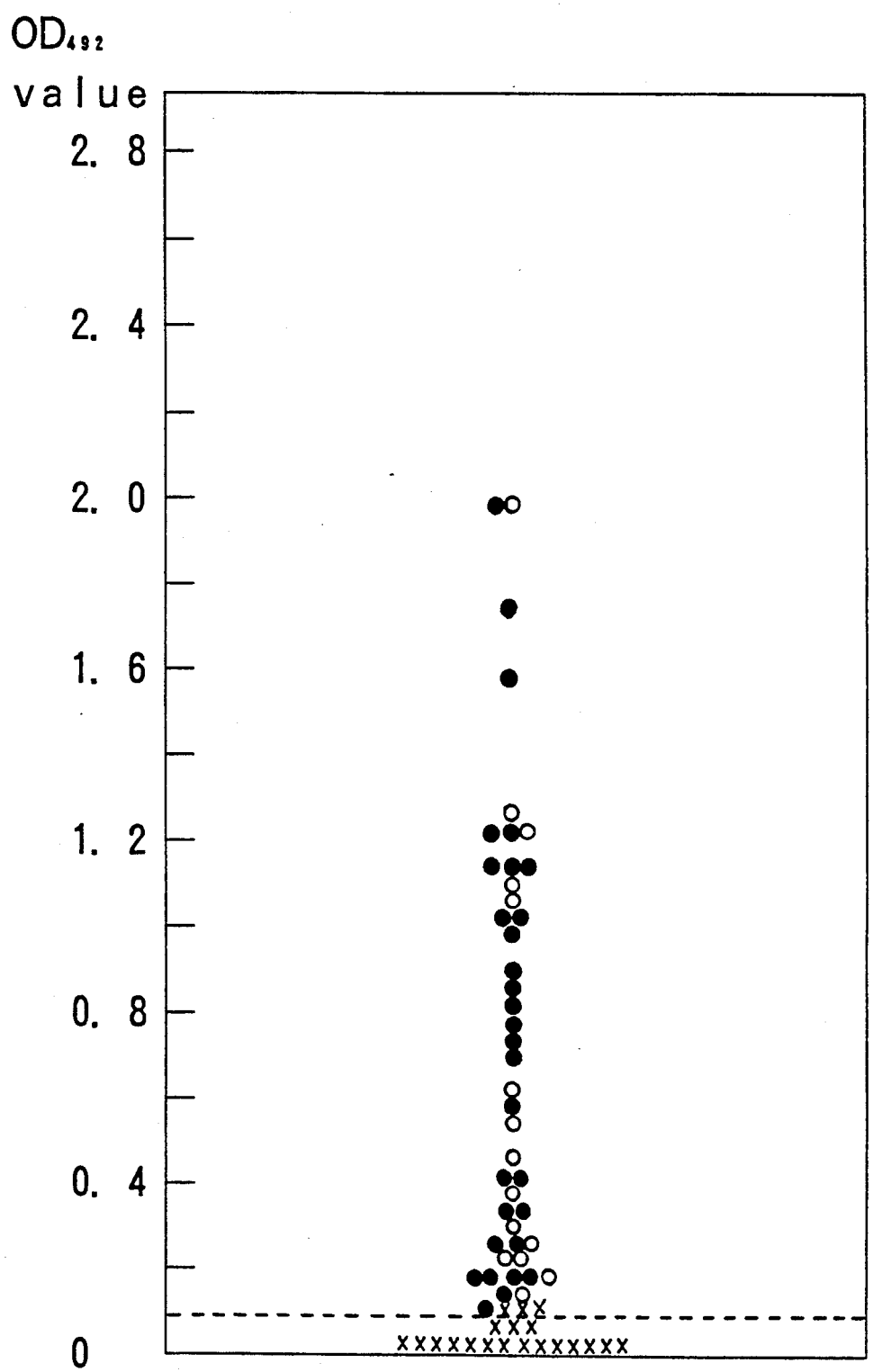
FIGS. 6, 7, 8, 9, 10 and 11 show the $OD_{492}$ value distributions obtained by assaying respective serum specimens by the method described in Example 9 using the peptides obtained in Examples 3, 4 and 5 and Reference Examples 4, 5 and 6, respectively.
Figure 7:
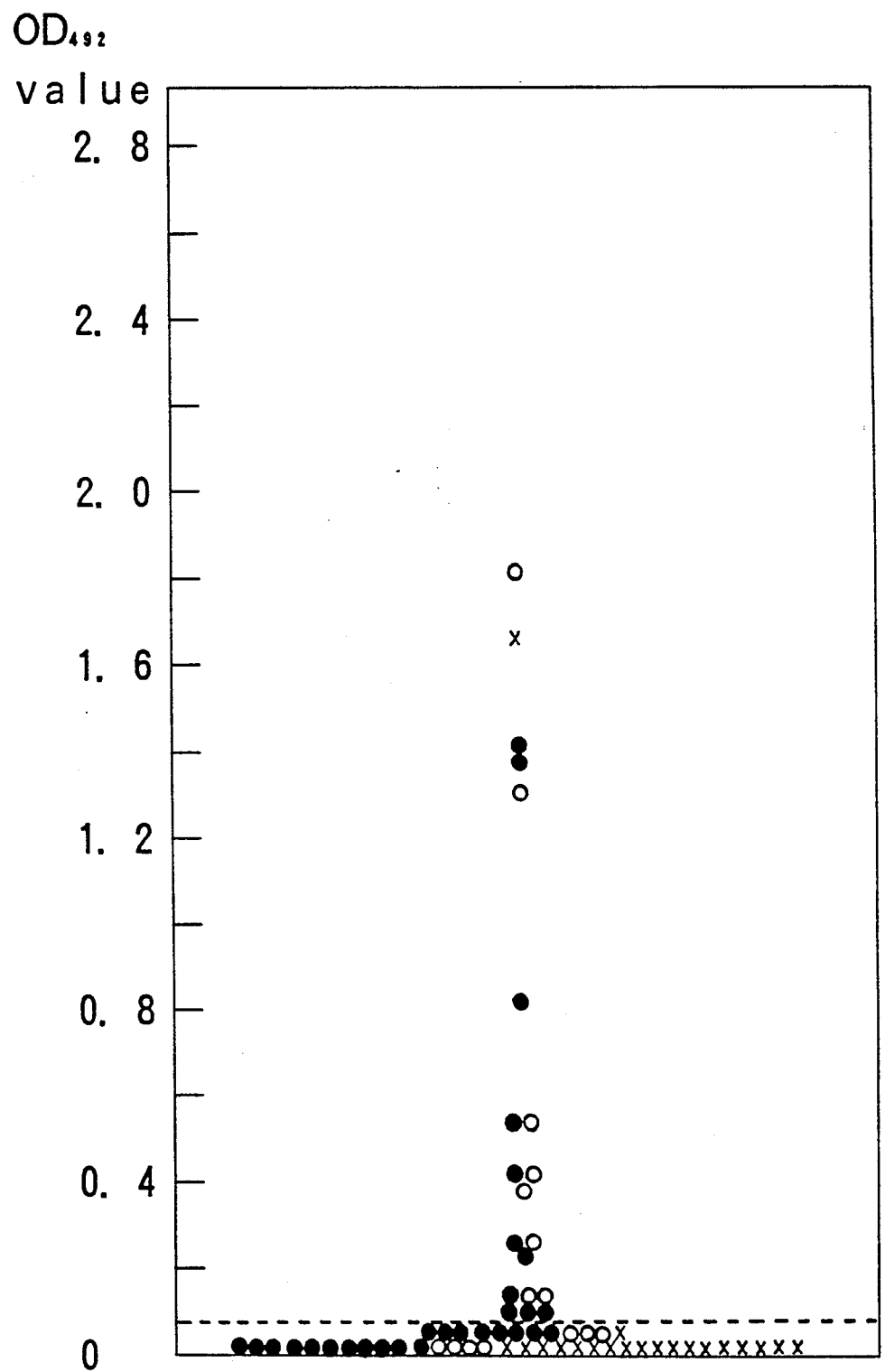
Figure 8:
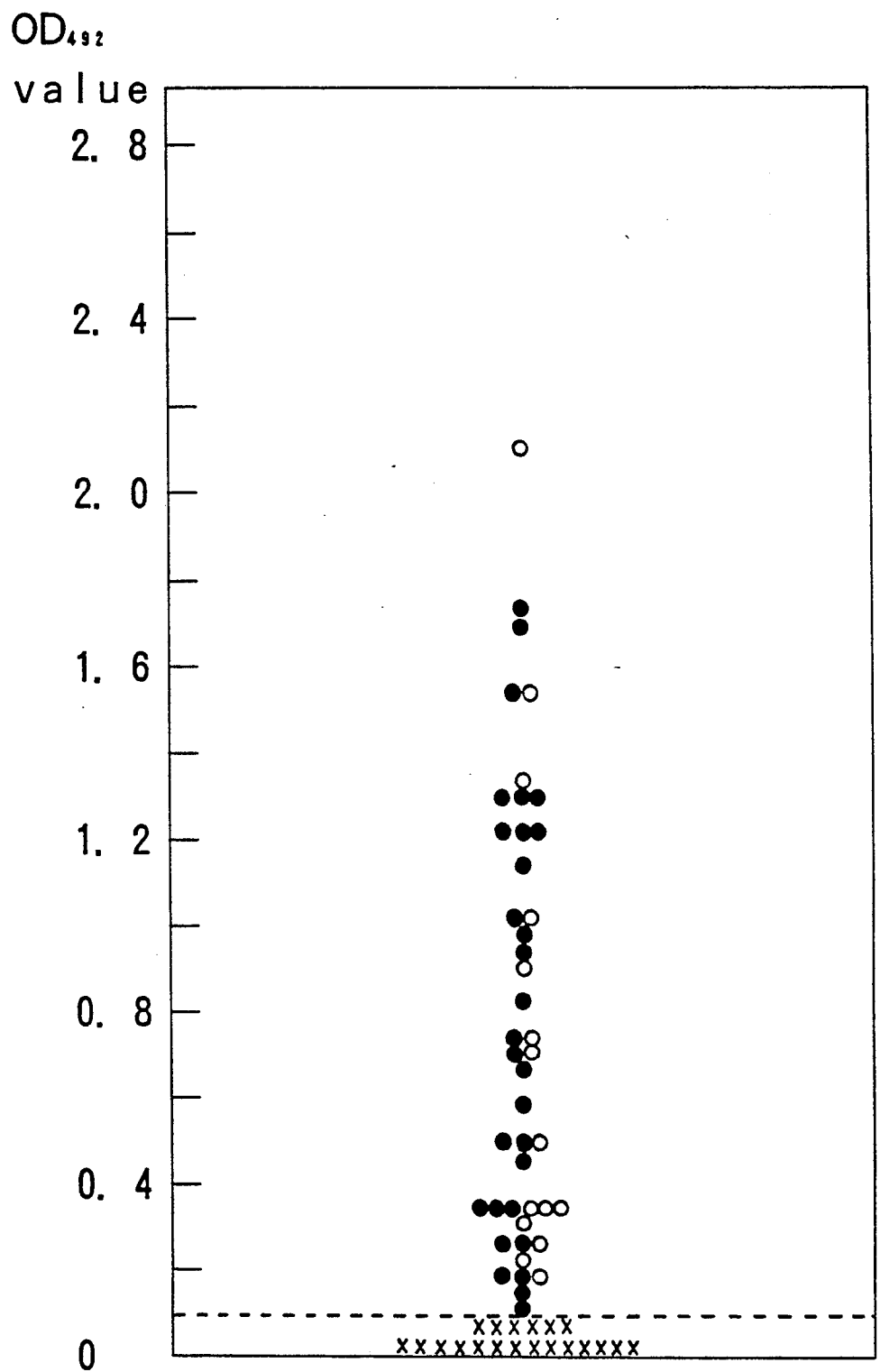
Figure 9:
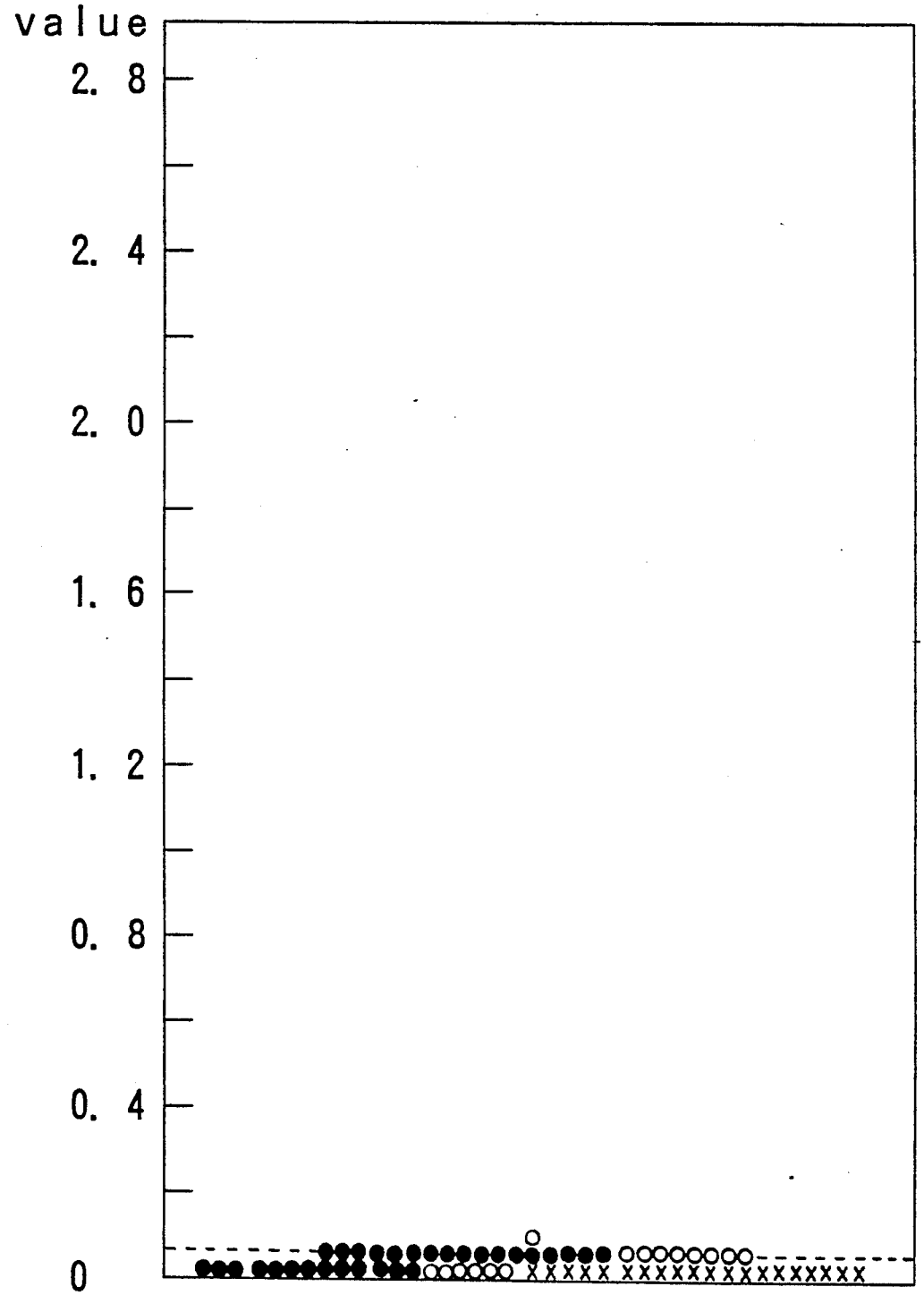
Figure 10:
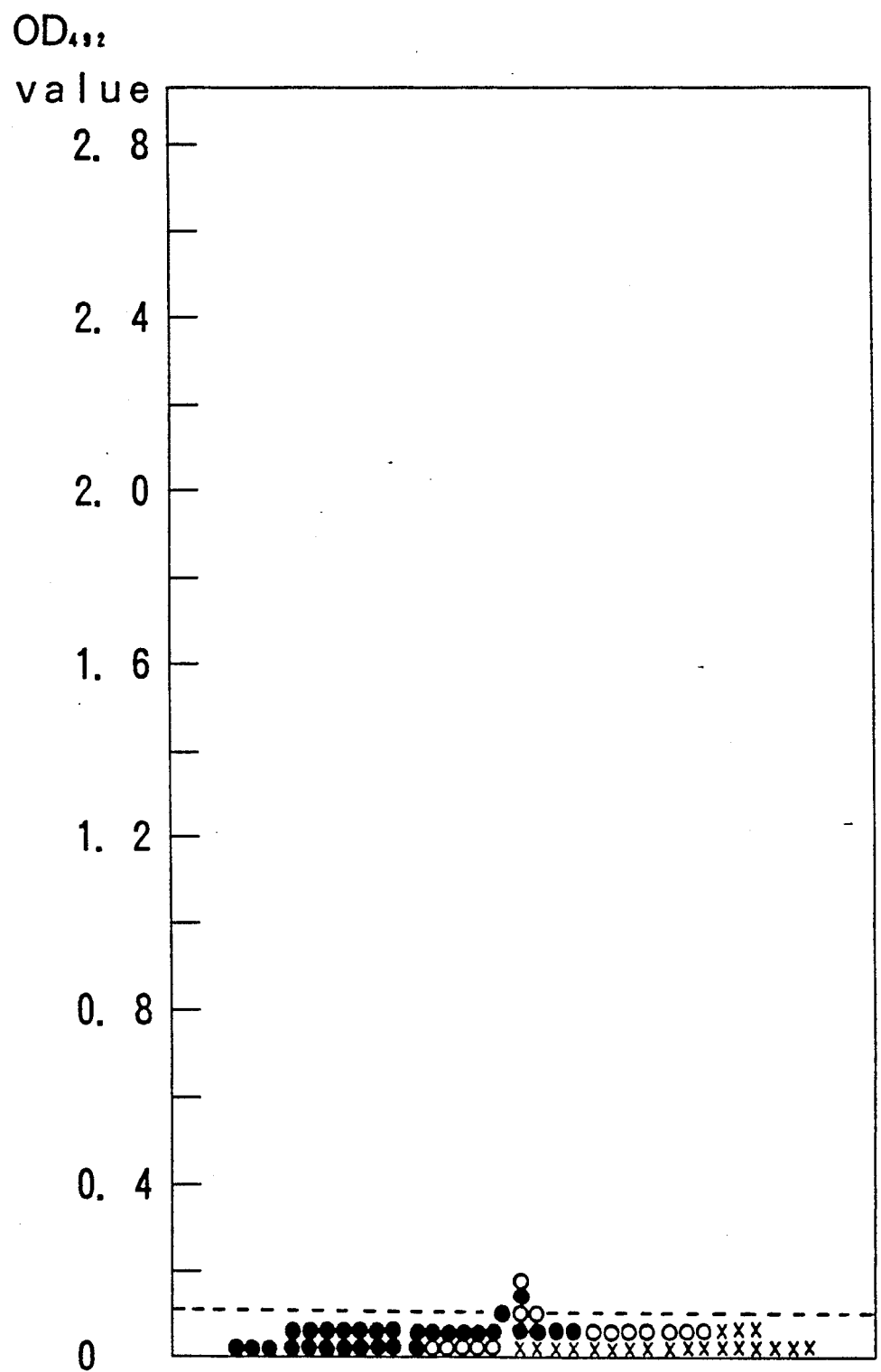
Figure 11:
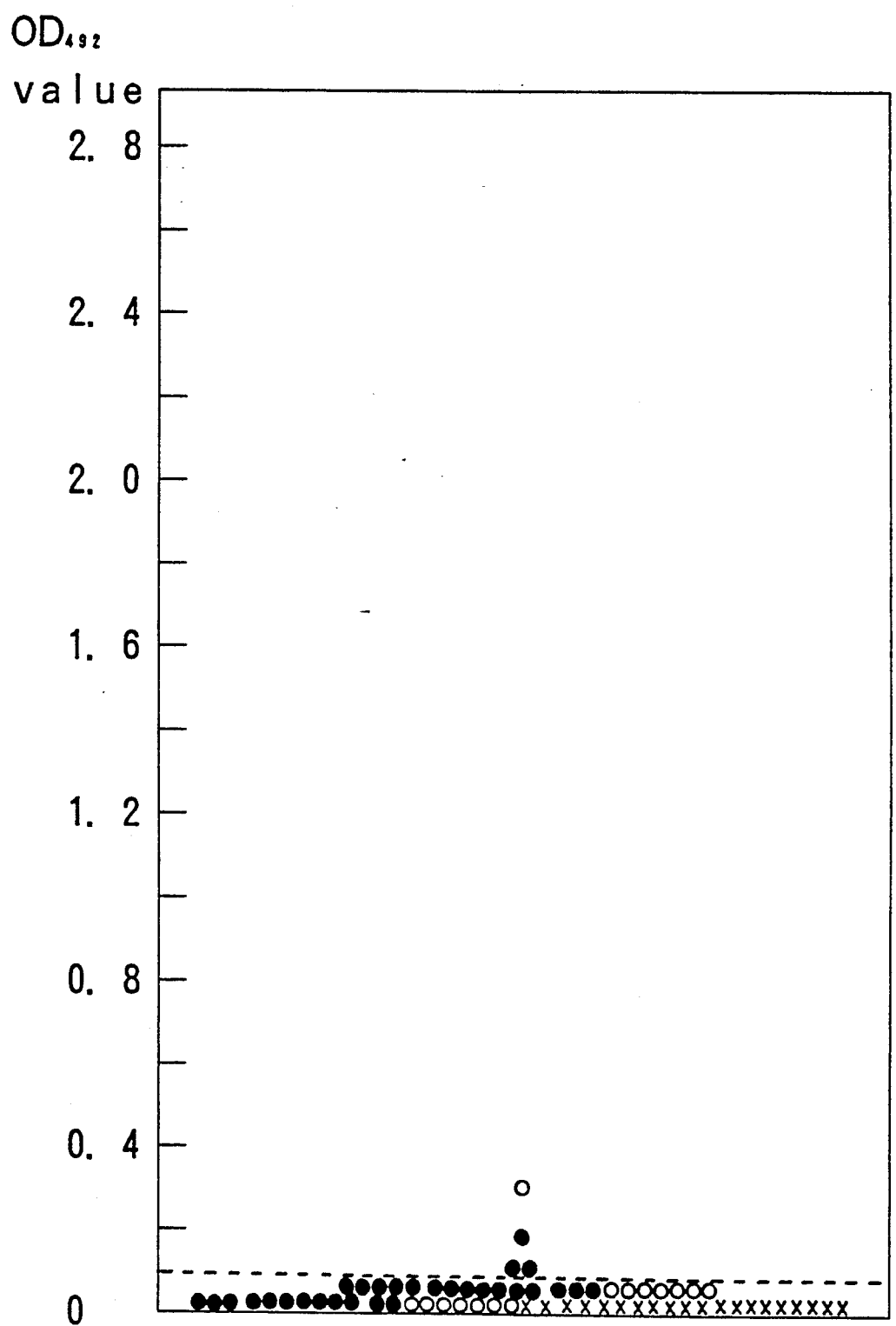

Assay results are given in Tables 8, 9, 10 and 11. Positive response ratios are given in Table 12. FIGS. 6-11 show each $OD_{492}$ value distribution. It is seen from Table 12 that serum A and serum B showed positive response ratios of 96.7% or 100%, respectively, when the peptide obtained in Example 3 or 5 was used for enzyme immunoassay, and serum C and normal human serum D showed a positive response ratio of 0% or a very low ratio. It was thus found that the enzyme immunoassay using these peptides offer high sensitivity and high specificity. Also, when the peptide obtained in Example 4 was used for enzyme immunoassay, serum A, serum B, serum C and serum D showed positive response ratios of 36.7%, 53.3%, 5.0% and 0.0%, respectively; the peptides used proved to have an antigenicity differing from that of the peptides obtained in Examples 3 and 5. Furthermore, when the peptides obtained in Reference Examples 4 through 6 were used for enzyme immunoassay, serum A, serum B, serum C and serum D showed a positive response ratio of 0% or a very low ratio. It was thus found that the enzyme immunoassay using these peptides is poor in sensitivity and specificity. These findings demonstrate that the use of the peptides obtained in Examples 3, 4 and 5 permits efficient judgement for the presence or absence of anti-HCV antibody.

TABLE 8

| | | Peptide obtained in Exam. 3 | Peptide obtained in Exam. 4 | Peptide obtained in Exam. 5 | Peptide obtained in Ref. Exam. 4 | Peptide obtained in Ref. Exam. 5 | Peptide obtained in Ref. Exam 6 |
|---|---|---|---|---|---|---|---|
| Serum A | 1 | 0.248 | 0.057 | 0.255 | 0.059 | 0.040 | 0.042 |
| | 2 | 0.156 | 0.041 | 0.178 | 0.052 | 0.043 | 0.051 |
| | 3 | 1.757 | 0.035 | 1.689 | 0.064 | 0.050 | 0.048 |
| | 4 | 1.220 | 0.021 | 1.214 | 0.032 | 0.031 | 0.034 |
| | 5 | 1.225 | 0.029 | 1.312 | 0.048 | 0.044 | 0.038 |
| | 6 | 0.688 | 0.100 | 0.593 | 0.026 | 0.044 | 0.044 |
| | 7 | 1.597 | 0.041 | 1.555 | 0.050 | 0.048 | 0.045 |
| | 8 | 0.766 | 0.277 | 0.821 | 0.041 | 0.055 | 0.045 |
| | 9 | 0.595 | 0.520 | 0.333 | 0.042 | 0.035 | 0.036 |
| | 10 | 0.742 | 0.038 | 0.673 | 0.031 | 0.040 | 0.036 |
| | 11 | 0.323 | 0.035 | 0.331 | 0.025 | 0.032 | 0.032 |
| | 12 | 0.877 | 0.058 | 0.758 | 0.027 | 0.033 | 0.038 |
| | 13 | 1.121 | 0.033 | 1.296 | 0.062 | 0.047 | 0.040 |
| | 14 | 0.999 | 0.034 | 1.009 | 0.030 | 0.026 | 0.030 |
| | 15 | 0.194 | 0.801 | 0.346 | 0.041 | 0.058 | 0.056 |
| | 16 | 0.834 | 1.397 | 1.215 | 0.037 | 0.112 | 0.056 |
| | 17 | 1.133 | 0.091 | 1.239 | 0.037 | 0.037 | 0.057 |
| | 18 | 0.249 | 0.053 | 0.269 | 0.051 | 0.057 | 0.081 |
| | 19 | 0.356 | 0.051 | 0.455 | 0.029 | 0.039 | 0.063 |
| | 20 | 0.185 | 0.032 | 0.123 | 0.052 | 0.033 | 0.031 |
| | 21 | 0.081 | 0.019 | 0.115 | 0.027 | 0.027 | 0.030 |
| | 22 | 0.415 | 0.119 | 0.489 | 0.061 | 0.058 | 0.189 |
| | 23 | 0.196 | 0.062 | 0.175 | 0.054 | 0.070 | 0.057 |
| | 24 | 0.887 | 0.036 | 0.965 | 0.059 | 0.045 | 0.067 |
| | 25 | 1.019 | 0.030 | 1.137 | 0.044 | 0.044 | 0.076 |
| | 26 | 1.120 | 0.202 | 1.284 | 0.042 | 0.035 | 0.026 |
| | 27 | 0.191 | 1.417 | 0.685 | 0.048 | 0.123 | 0.065 |
| | 28 | 1.005 | 0.420 | 0.951 | 0.026 | 0.060 | 0.026 |
| | 29 | 1.969 | 0.062 | 1.736 | 0.039 | 0.045 | 0.112 |
| | 30 | 0.406 | 0.155 | 0.514 | 0.036 | 0.035 | 0.036 |

TABLE 9

| | | Peptide obtained in Exam. 3 | Peptide obtained in Exam. 4 | Peptide obtained in Exam. 5 | Peptide obtained in Ref. Exam. 4 | Peptide obtained in Ref. Exam. 5 | Peptide obtained in Ref. Exam 6 |
|---|---|---|---|---|---|---|---|
| Serum B | 1 | 1.057 | 0.394 | 1.003 | 0.049 | 0.111 | 0.036 |
| | 2 | 0.468 | 0.027 | 0.695 | 0.052 | 0.032 | 0.025 |
| | 3 | 0.602 | 1.302 | 0.738 | 0.036 | 0.071 | 0.285 |
| | 4 | 0.548 | 0.149 | 0.489 | 0.038 | 0.049 | 0.029 |
| | 5 | 0.188 | 0.026 | 0.216 | 0.034 | 0.038 | 0.034 |
| | 6 | 0.233 | 1.804 | 0.356 | 0.035 | 0.190 | 0.051 |
| | 7 | 1.243 | 0.261 | 1.546 | 0.057 | 0.085 | 0.061 |
| | 8 | 0.246 | 0.019 | 0.359 | 0.025 | 0.019 | 0.020 |
| | 9 | 1.987 | 0.054 | 2.106 | 0.043 | 0.040 | 0.060 |
| | 10 | 0.124 | 0.044 | 0.321 | 0.042 | 0.031 | 0.043 |
| | 11 | 1.095 | 0.421 | 0.895 | 0.044 | 0.079 | 0.077 |
| | 12 | 0.375 | 0.030 | 0.269 | 0.050 | 0.056 | 0.049 |
| | 13 | 0.286 | 0.531 | 0.199 | 0.037 | 0.054 | 0.024 |
| | 14 | 1.229 | 0.063 | 1.359 | 0.085 | 0.045 | 0.076 |
| | 15 | 0.237 | 0.150 | 0.316 | 0.041 | 0.037 | 0.037 |

TABLE 10

| | | Peptide obtained in Exam. 3 | Peptide obtained in Exam. 4 | Peptide obtained in Exam. 5 | Peptide obtained in Ref. Exam. 4 | Peptide obtained in Ref. Exam. 5 | Peptide obtained in Ref. Exam 6 |
|---|---|---|---|---|---|---|---|
| Serum C | 1 | 0.096 | 0.024 | 0.055 | 0.022 | 0.024 | 0.017 |
| | 2 | 0.042 | 0.060 | 0.050 | 0.027 | 0.045 | 0.024 |
| | 3 | 0.034 | 0.035 | 0.024 | 0.015 | 0.034 | 0.107 |
| | 4 | 0.048 | 0.037 | 0.040 | 0.018 | 0.033 | 0.015 |
| | 5 | 0.039 | 0.034 | 0.030 | 0.026 | 0.037 | 0.016 |
| | 6 | 0.039 | 0.025 | 0.033 | 0.016 | 0.035 | 0.021 |
| | 7 | 0.026 | 0.031 | 0.026 | 0.033 | 0.031 | 0.014 |
| | 8 | 0.029 | 0.026 | 0.039 | 0.021 | 0.026 | 0.009 |
| | 9 | 0.036 | 0.027 | 0.035 | 0.017 | 0.027 | 0.015 |
| | 10 | 0.023 | 0.032 | 0.031 | 0.024 | 0.034 | 0.027 |
| | 11 | 0.020 | 0.034 | 0.022 | 0.029 | 0.042 | 0.024 |
| | 12 | 0.029 | 0.022 | 0.055 | 0.018 | 0.023 | 0.011 |
| | 13 | 0.095 | 0.032 | 0.048 | 0.035 | 0.035 | 0.015 |
| | 14 | 0.023 | 0.026 | 0.043 | 0.017 | 0.026 | 0.011 |
| | 15 | 0.022 | 0.025 | 0.037 | 0.014 | 0.024 | 0.015 |
| | 16 | 0.020 | 0.025 | 0.026 | 0.015 | 0.024 | 0.013 |
| | 17 | 0.030 | 0.026 | 0.027 | 0.013 | 0.034 | 0.014 |
| | 18 | 0.040 | 0.034 | 0.030 | 0.017 | 0.037 | 0.017 |
| | 19 | 0.016 | 0.023 | 0.020 | 0.024 | 0.031 | 0.010 |
| | 20 | 0.095 | 1.675 | 0.020 | 0.031 | 0.044 | 0.015 |

TABLE 11

| | | Peptide obtained in Exam. 3 | Peptide obtained in Exam. 4 | Peptide obtained in Exam. 5 | Peptide obtained in Ref. Exam. 4 | Peptide obtained in Ref. Exam. 5 | Peptide obtained in Ref. Exam 6 |
|---|---|---|---|---|---|---|---|
| Serum D | 1 | 0.072 | 0.050 | 0.053 | 0.052 | 0.074 | 0.047 |
| | 2 | 0.072 | 0.060 | 0.053 | 0.051 | 0.057 | 0.045 |

TABLE 11-continued

|   | Peptide obtained in Exam. 3 | Peptide obtained in Exam. 4 | Peptide obtained in Exam. 5 | Peptide obtained in Ref. Exam. 4 | Peptide obtained in Ref. Exam. 5 | Peptide obtained in Ref. Exam 6 |
|---|---|---|---|---|---|---|
| 3 | 0.061 | 0.053 | 0.099 | 0.059 | 0.093 | 0.066 |
| 4 | 0.089 | 0.064 | 0.064 | 0.053 | 0.068 | 0.059 |
| 5 | 0.056 | 0.056 | 0.060 | 0.055 | 0.057 | 0.056 |
| 6 | 0.052 | 0.050 | 0.065 | 0.049 | 0.068 | 0.083 |
| 7 | 0.058 | 0.051 | 0.060 | 0.050 | 0.059 | 0.045 |
| 8 | 0.065 | 0.060 | 0.055 | 0.046 | 0.105 | 0.051 |
| 9 | 0.067 | 0.069 | 0.063 | 0.045 | 0.064 | 0.068 |
| 10 | 0.078 | 0.064 | 0.047 | 0.041 | 0.045 | 0.055 |
| X | 0.067 | 0.058 | 0.062 | 0.050 | 0.069 | 0.058 |
| SD | 0.011 | 0.007 | 0.014 | 0.005 | 0.018 | 0.012 |
| X + 2SD | 0.089 | 0.072 | 0.090 | 0.060 | 0.105 | 0.082 |

TABLE 12

| Example No. of peptide used | Positive ratio of serum A (%) | Positive ratio of serum B (%) | Positive ratio of serum C (%) | Positive ratio of serum D (%) |
|---|---|---|---|---|
| Example 3 | 96.7 (29/30) | 100.0 (15/15) | 15.0 (3/20) | 10.0 (1/10) |
| Example 4 | 36.7 (11/30) | 53.3 (8/15) | 5.0 (1/20) | 0.0 (0/10) |
| Example 5 | 100.0 (30/30) | 100.0 (15/15) | 0.0 (0/20) | 10.0 (1/10) |
| Ref. Exam. 4 | 10.0 (3/30) | 6.7 (1/15) | 0.0 (0/20) | 0.0 (0/10) |
| Ref. Exam. 5 | 6.7 (2/30) | 13.3 (2/15) | 0.0 (0/20) | 10.0 (1/10) |
| Ref. Exam. 6 | 6.7 (2/30) | 6.7 (1/15) | 0.0 (0/20) | 10.0 (1/10) |

Example 11

Using the peptides obtained in Examples 6, 7 and 8 and Reference Example 7 as antigens, determination was made by enzyme immunoassay in the same manner as in Example 9.

Figure 12:
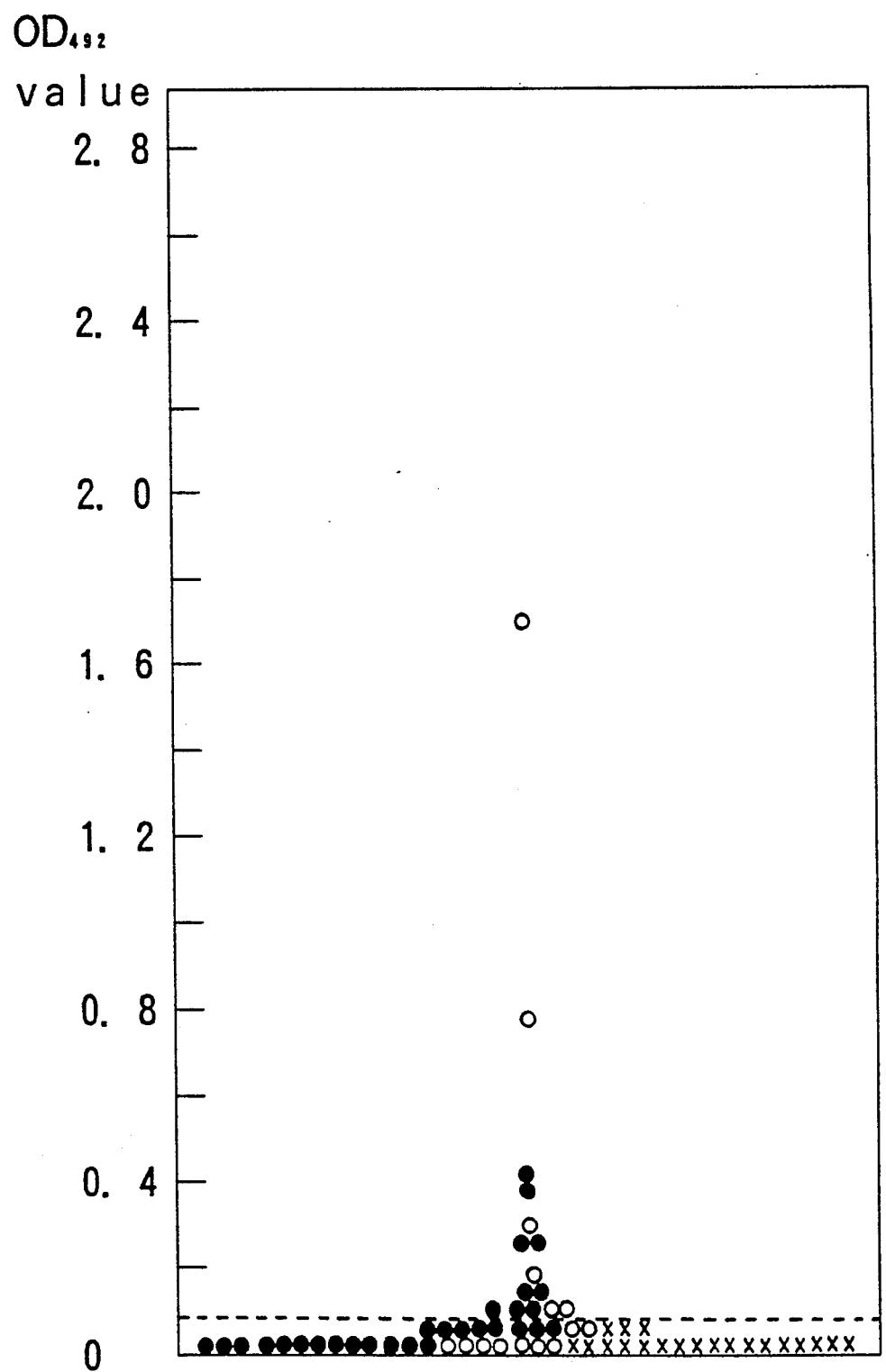
FIGS. 12, 13, 14 and 15 show the $OD_{492}$ value distributions obtained by assaying respective serum specimens by the method described in Example 9 using the peptides obtained in Examples 6, 7 and 8 and Reference Example 7, respectively.
Figure 13:
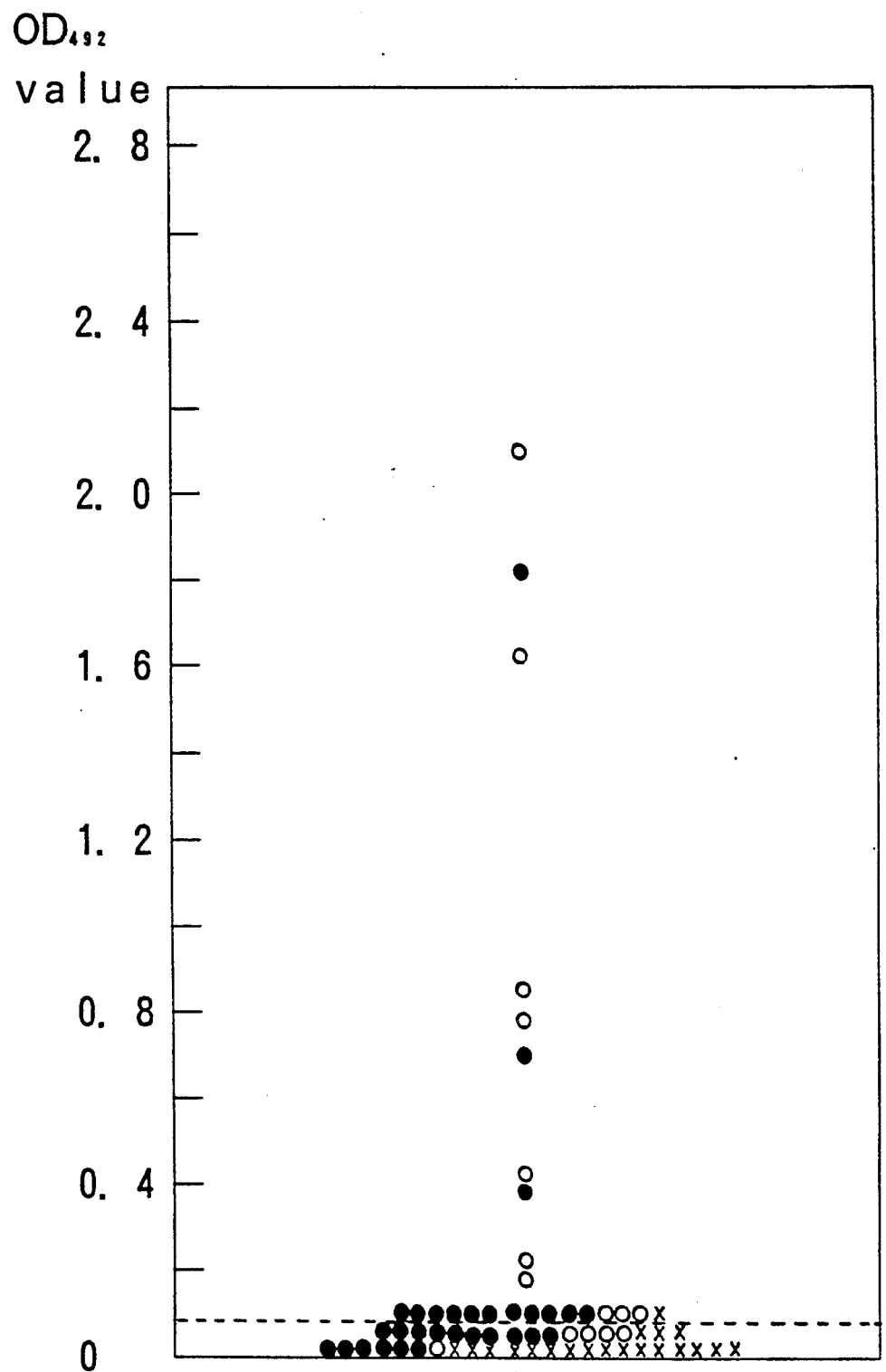
Figure 14:
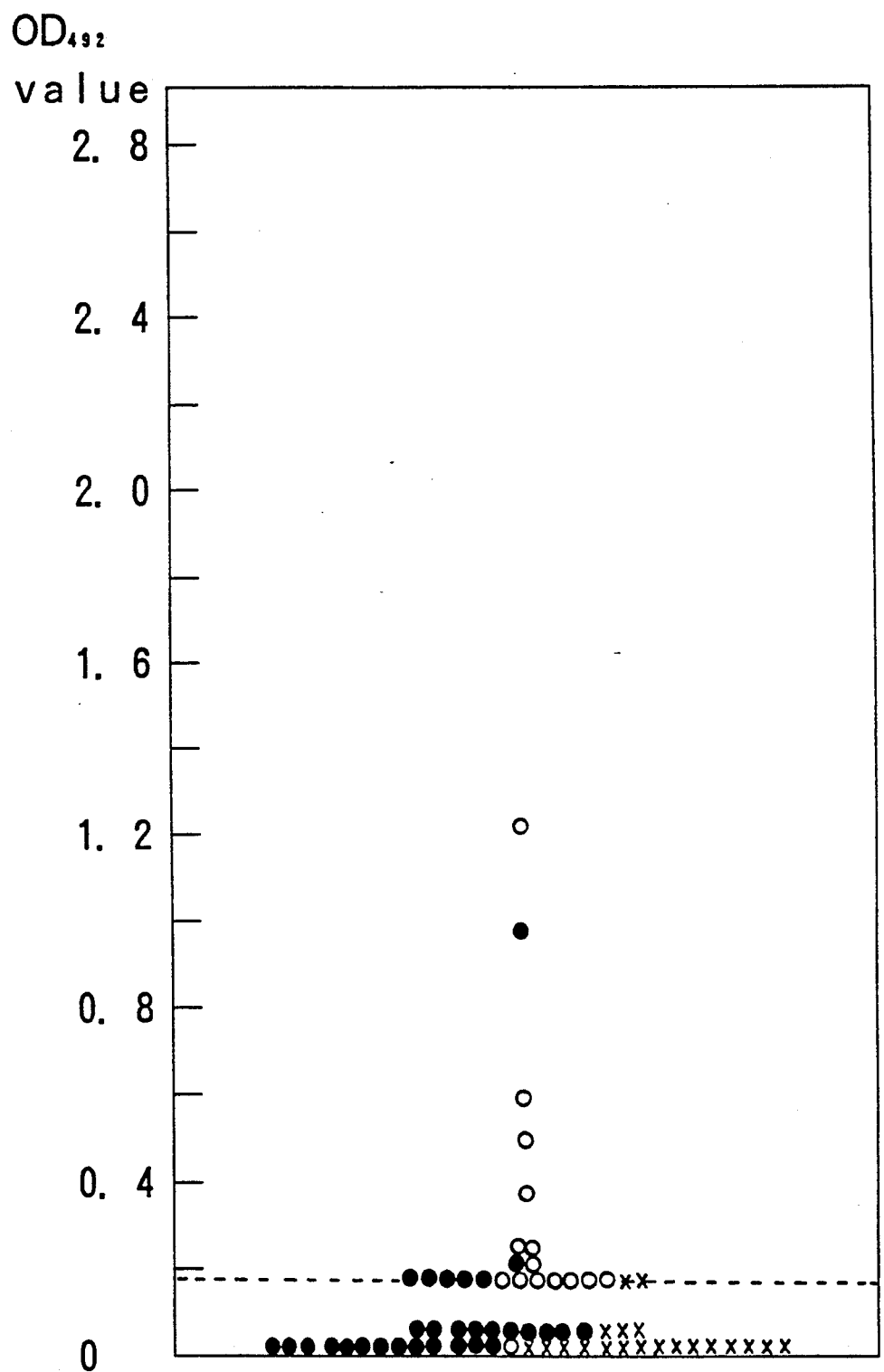
Figure 15:
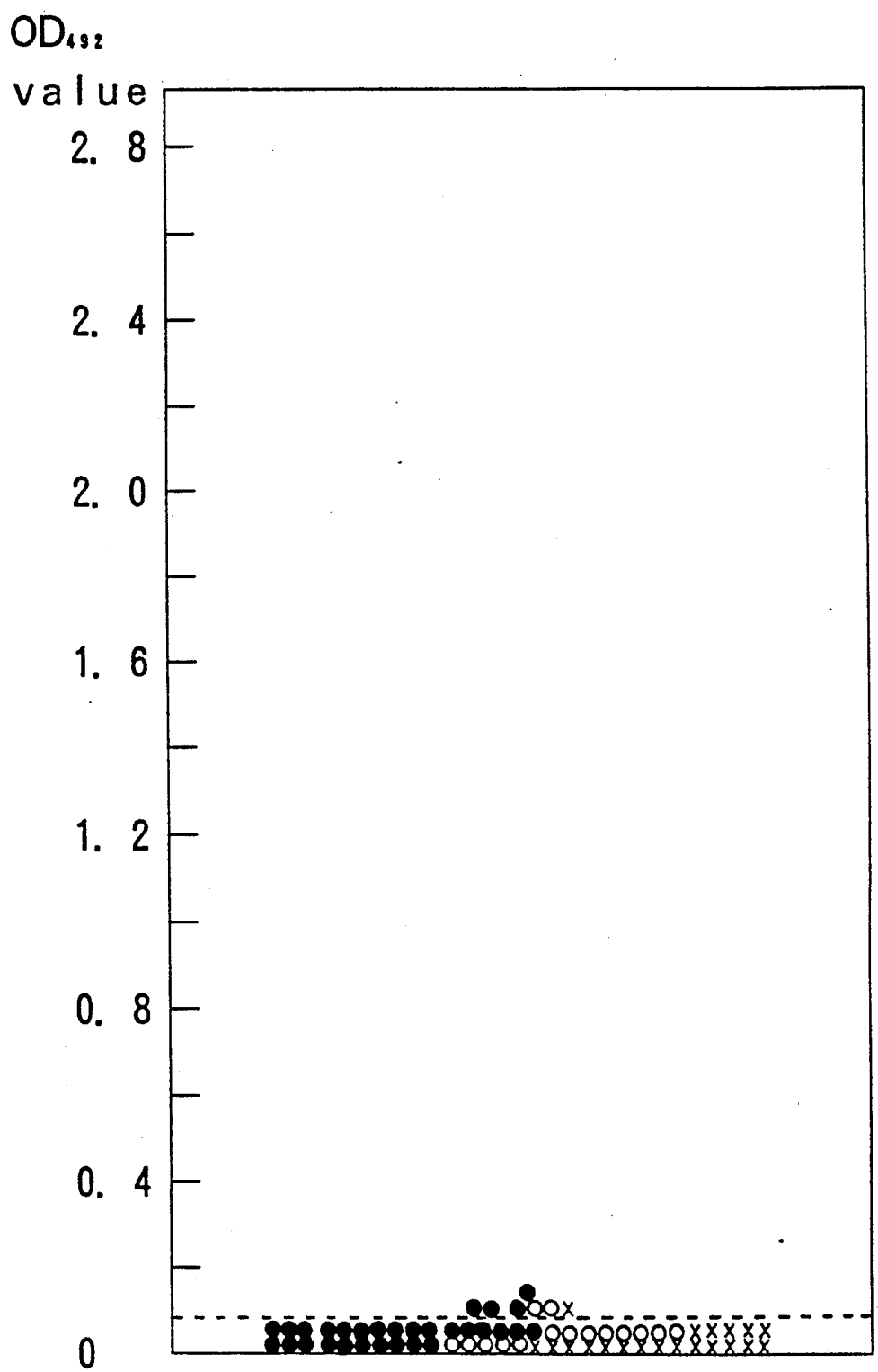

Assay results are given in Tables 13, 14, 15 and 16. Positive response ratios are given in Table 17. FIGS. 12-15 show each $OD_{492}$ value distribution. It is seen from Table 17 that when the peptide obtained in Example 6 was used for enzyme immunoassay, serum A, serum B, serum C and normal human serum D showed positive response ratios of 33.3%, 40.0%, 0% and 0%, respectively. When the peptide obtained in Example 7 was used for enzyme immunoassay, serum A, serum B, serum C and normal human serum D showed positive response ratios of 50.0%, 66.7%, 5.0% and 0%, respectively. When the peptide obtained in Example 8 was used for enzyme immunoassay, serum A, serum B, serum C and normal human serum D showed positive response ratios of 23.3%, 93.3%, 5.0% and 10.0%, respectively. The enzyme immunoassay using these peptides proved to be closely correlated to the immunoscreening method described in Reference Example 8, which uses #8 clone, #14 clone and #18 clone, cloned from the ribonucleic acid isolated by several researchers including one of the present inventors. Also, when the peptide obtained in Reference Example 7 was used for enzyme immunoassay, serum A, serum B, serum C and serum D showed positive response ratios of 13.3%, 13.3%, 5.0% and 0.0%, respectively. The peptides used proved to have an antigenicity differing from that of the peptides obtained in Examples 6, 7 and 8. These findings demonstrate that the use of the peptides obtained in Examples 6, 7 and 8 permits efficient judgement for the presence or absence of anti-HCV antibody.

TABLE 13

|  |  | Peptide obtained in Exam. 6 | Peptide obtained in Exam. 7 | Peptide obtained in Exam. 8 | Peptide obtained in Ref. Exam. 7 |
|---|---|---|---|---|---|
| Serum A | 1 | 0.379 | 0.049 | 0.053 | 0.045 |
|  | 2 | 0.040 | 0.066 | 0.233 | 0.044 |
|  | 3 | 0.094 | 0.087 | 0.043 | 0.093 |
|  | 4 | 0.029 | 0.037 | 0.024 | 0.029 |
|  | 5 | 0.035 | 0.085 | 0.040 | 0.034 |
|  | 6 | 0.033 | 0.036 | 0.021 | 0.025 |
|  | 7 | 0.045 | 0.051 | 0.172 | 0.047 |
|  | 8 | 0.031 | 0.047 | 0.036 | 0.042 |
|  | 9 | 0.032 | 0.094 | 0.046 | 0.043 |
|  | 10 | 0.030 | 0.037 | 0.023 | 0.036 |
|  | 11 | 0.034 | 0.048 | 0.029 | 0.034 |
|  | 12 | 0.038 | 0.042 | 0.026 | 0.040 |
|  | 13 | 0.079 | 0.094 | 0.050 | 0.044 |
|  | 14 | 0.039 | 0.030 | 0.053 | 0.023 |
|  | 15 | 0.279 | 0.083 | 0.038 | 0.042 |
|  | 16 | 0.041 | 1.824 | 0.980 | 0.040 |
|  | 17 | 0.040 | 0.079 | 0.193 | 0.046 |
|  | 18 | 0.081 | 0.368 | 0.184 | 0.131 |
|  | 19 | 0.124 | 0.683 | 0.197 | 0.030 |
|  | 20 | 0.032 | 0.054 | 0.195 | 0.047 |
|  | 21 | 0.027 | 0.028 | 0.019 | 0.023 |
|  | 22 | 0.409 | 0.097 | 0.048 | 0.099 |
|  | 23 | 0.121 | 0.096 | 0.042 | 0.053 |
|  | 24 | 0.084 | 0.082 | 0.055 | 0.109 |
|  | 25 | 0.048 | 0.045 | 0.032 | 0.034 |
|  | 26 | 0.030 | 0.052 | 0.026 | 0.042 |
|  | 27 | 0.041 | 0.101 | 0.054 | 0.049 |
|  | 28 | 0.026 | 0.039 | 0.022 | 0.037 |
|  | 29 | 0.043 | 0.095 | 0.036 | 0.051 |
|  | 30 | 0.242 | 0.093 | 0.028 | 0.045 |

TABLE 14

|  |  | Peptide obtained in Exam. 6 | Peptide obtained in Exam. 7 | Peptide obtained in Exam. 8 | Peptide obtained in Ref. Exam. 7 |
|---|---|---|---|---|---|
| Serum B | 1 | 0.039 | 0.095 | 0.187 | 0.047 |
|  | 2 | 0.098 | 0.092 | 0.184 | 0.051 |
|  | 3 | 0.026 | 0.050 | 0.489 | 0.040 |
|  | 4 | 0.033 | 0.432 | 0.377 | 0.046 |
|  | 5 | 0.030 | 0.042 | 0.174 | 0.036 |
|  | 6 | 0.783 | 2.083 | 1.217 | 0.044 |
|  | 7 | 0.189 | 1.608 | 0.579 | 0.050 |
|  | 8 | 0.020 | 0.027 | 0.030 | 0.020 |
|  | 9 | 0.044 | 0.045 | 0.194 | 0.037 |
|  | 10 | 0.027 | 0.864 | 0.175 | 0.035 |
|  | 11 | 0.282 | 0.049 | 0.190 | 0.052 |
|  | 12 | 0.047 | 0.109 | 0.199 | 0.096 |
|  | 13 | 0.034 | 0.762 | 0.244 | 0.036 |
|  | 14 | 0.088 | 0.210 | 0.204 | 0.109 |
|  | 15 | 1.684 | 0.160 | 0.267 | 0.050 |

TABLE 15

|  |  | Peptide obtained in Exam. 6 | Peptide obtained in Exam. 7 | Peptide obtained in Exam. 8 | Peptide obtained in Ref. Exam. 7 |
|---|---|---|---|---|---|
| Serum C | 1 | 0.027 | 0.028 | 0.030 | 0.028 |
|  | 2 | 0.016 | 0.055 | 0.037 | 0.089 |
|  | 3 | 0.017 | 0.027 | 0.025 | 0.033 |
|  | 4 | 0.041 | 0.038 | 0.048 | 0.032 |
|  | 5 | 0.015 | 0.037 | 0.045 | 0.041 |
|  | 6 | 0.025 | 0.021 | 0.033 | 0.026 |
|  | 7 | 0.028 | 0.085 | 0.035 | 0.051 |
|  | 8 | 0.042 | 0.028 | 0.026 | 0.033 |
|  | 9 | 0.018 | 0.021 | 0.040 | 0.029 |
|  | 10 | 0.019 | 0.034 | 0.022 | 0.040 |
|  | 11 | 0.018 | 0.025 | 0.021 | 0.034 |
|  | 12 | 0.010 | 0.026 | 0.019 | 0.028 |
|  | 13 | 0.022 | 0.042 | 0.171 | 0.045 |

TABLE 15-continued

|  | Peptide obtained in Exam. 6 | Peptide obtained in Exam. 7 | Peptide obtained in Exam. 8 | Peptide obtained in Ref. Exam. 7 |
|---|---|---|---|---|
| 14 | 0.051 | 0.030 | 0.018 | 0.029 |
| 15 | 0.017 | 0.024 | 0.019 | 0.025 |
| 16 | 0.038 | 0.025 | 0.020 | 0.029 |
| 17 | 0.025 | 0.022 | 0.025 | 0.023 |
| 18 | 0.022 | 0.020 | 0.021 | 0.032 |
| 19 | 0.028 | 0.024 | 0.023 | 0.029 |
| 20 | 0.022 | 0.047 | 0.176 | 0.053 |

TABLE 16

|  |  | Peptide obtained in Exam. 6 | Peptide obtained in Exam. 7 | Peptide obtained in Exam. 8 | Peptide obtained in Ref. Exam. 7 |
|---|---|---|---|---|---|
| Serum D | 1 | 0.051 | 0.054 | 0.047 | 0.062 |
|  | 2 | 0.062 | 0.051 | 0.079 | 0.057 |
|  | 3 | 0.068 | 0.067 | 0.063 | 0.075 |
|  | 4 | 0.052 | 0.074 | 0.143 | 0.077 |
|  | 5 | 0.060 | 0.059 | 0.183 | 0.079 |
|  | 6 | 0.063 | 0.058 | 0.055 | 0.070 |
|  | 7 | 0.061 | 0.060 | 0.051 | 0.071 |
|  | 8 | 0.063 | 0.060 | 0.073 | 0.068 |
|  | 9 | 0.065 | 0.070 | 0.059 | 0.080 |
|  | 10 | 0.050 | 0.051 | 0.064 | 0.064 |
| X |  | 0.060 | 0.060 | 0.082 | 0.070 |
| SD |  | 0.006 | 0.008 | 0.045 | 0.008 |
| X + 2SD |  | 0.072 | 0.076 | 0.171 | 0.086 |

TABLE 17

| Example No. of peptide used | Positive ratio of serum A (%) | Positive ratio of serum B (%) | Positive ratio of serum C (%) | Positive ratio of serum D (%) |
|---|---|---|---|---|
| Example 6 | 33.3 (10/30) | 40.0 (6/15) | 0.0 (0/20) | 0.0 (0.10) |
| Example 7 | 50.0 (15/30) | 66.7 (10/15) | 5.0 (1/20) | 0.0 (0/10) |
| Example 8 | 23.3 (7/30) | 93.3 (14/15) | 5.0 (1/20) | 10.0 (1/10) |
| Ref. Exam. 7 | 13.3 (4/30) | 13.3 (2/15) | 5.0 (1/20) | 0.0 (0/10) |

Example 12

Subject samples

Table 18 lists the diseases from which the serum specimens used were derived and the number of specimens for each disease.

TABLE 18

| Disease | Symptom | Number of specimens |
|---|---|---|
| Hepatitis of the sporadic non-A, non-B type | acute, acme | 1 |
| Hepatitis of the sporadic non-A, non-B type | acute, recovery stage | 1 |
| Hepatitis of the sporadic non-A, non-B type | chronic | 1 |
| Hepatitis of the sporadic non-A, non-B type | chronic (liver cirrhosis) | 1 |
| hepatitis of the post-transfusion non-A, non-B type | acute, acme | 1 |
| hepatitis of the post-transfusion non-A, non-B type | acute, recovery stage | 2 |
| hepatitis of the post-transfusion non-A, non-B type | chronic | 1 |
| hepatitis of the post-transfusion non-A, non-B type | chronic (liver cancer) | 1 |
| alcoholic hepatitis | chronic | 2 |
| hepatitis B | chronic | 3 |
| Normal human serum |  | 10 |

Determination by enzyme immunoassay

The serum specimens listed in Table 18 were each examined for anti-HCV antibody by determining the absorbance by the following enzyme immunoassay procedure.

Specifically, the peptides obtained in Examples 1 and 2 and Reference Examples 1, 2 and 3, as antigens, were coated on assay microcups in the same manner as in Example 9, followed by reaction with each of the serum specimens listed in Table 18, and the absorbance at 492 nm ($OD_{492}$) of the reaction mixture containing the pigment formed from the coloring agent was determined.

Results

Assay results are given in Tables 19 and 20. The results are given for serum specimens in Table 18 assayed by enzyme immunoassay using the peptides obtained in Examples 1 and 2 in Table 19 and Reference Examples 1 through 3 in Table 20, respectively. Also, a cut-off value was set from the $OD_{492}$ value of 10 specimens of normal human serum, based on which the response to anti-HCV antibody was judged to be positive or negative. The cut-off value was calculated using the equation:

Cut-off value = mean $OD_{492}$ value of normal human serum + 2SD

Results of judgement for positive or negative response obtained on the basis of the cut-off value calculated from the results of normal serum specimens listed in Tables 19 and 20 are also given in Tables 19 and 20. It is seen from Table 19 that when the peptide obtained in Example 1 was used for enzyme immunoassay, the sera of patients of acute hepatitis in the recovery stage and chronic hepatitis of the sporadic non-A, non-B type, and the sera of patients of acute hepatitis in the acme and chronic hepatitis of the post-transfusion non-A, non-B type were judged to be positive for anti-HCV antibody. The sera of alcoholic hepatitis patients, the sera of hepatitis B patients and the sera of normal subjects were judged to be negative for anti-HCV antibody. When the peptide obtained in Example 2 was used for enzyme immunoassay, the sera of non-A, non-B chronic hepatitis patients were judged to be positive for anti-HCV antibody, and the sera of alcoholic hepatitis patients, the sera of hepatitis B patients and the sera of normal subjects were judged to be negative for anti-HCV antibody. These findings demonstrate that the enzyme immunoassay using the peptides obtained in Examples 1 and 2 is useful in early diagnosis of non-A, non-B hepatitis. Also, when the peptides obtained in Reference Examples 1, 2 and 3 were used for enzyme immunoassay, some of the sera of non-A, non-B hepatitis patients were judged to be negative for anti-HCV antibody, and some of the sera of hepatitis B patients and those of normal subjects were judged to be positive for anti-HCV antibody, i.e., the specificity and sensitivity were poor. In other words, the results of judgment by the enzyme immunoassay using the peptides obtained in Reference Examples 1, 2 and 3 involved false negative and false positive cases, demonstrating that the diagnostic efficiency for non-A, non-B hepatitis using these peptides is poor. These findings demonstrate that the use of the peptides obtained in Examples 1 and 2 permits efficient judgement for the presence or absence of anti-HCV antibody.

TABLE 19

| Classification of symptom | Peptide obtained in Example 1 OD | Judge | Peptide obtained in Example 2 OD | Judge |
|---|---|---|---|---|
| Hepatitis of sporadic | | | | |
| 1 acute, acme | 0.073 | − | 0.080 | + |
| 2 acute, recovery | 0.118 | + | 0.211 | + |
| 3 chronic | 2.250 | + | 2.216 | + |
| | 1.246 | + | 1.186 | + |
| Hepatitis of post-transfusion | | | | |
| 4 acute, acme | 0.456 | + | 0.348 | + |
| 5 acute, recovery | 0.056 | − | 0.089 | + |
| | 2.293 | + | 2.225 | + |
| 6 chronic | 0.169 | + | 0.154 | + |
| | 2.089 | + | 2.103 | + |
| Alcoholic hepatitis | | | | |
| 7 chronic | 0.048 | − | 0.057 | − |
| | 0.033 | − | 0.041 | − |
| Hepatitis B | | | | |
| 8 chronic | 0.078 | − | 0.075 | − |
| | 0.079 | − | 0.076 | − |
| | 0.047 | − | 0.045 | − |
| Normal human serum | | | | |
| 9 | 0.039 | − | 0.029 | − |
| | 0.038 | − | 0.045 | − |
| | 0.071 | − | 0.042 | − |
| | 0.057 | − | 0.043 | − |
| | 0.046 | − | 0.056 | − |
| | 0.070 | − | 0.063 | − |
| | 0.072 | − | 0.072 | − |
| | 0.043 | − | 0.044 | − |
| | 0.055 | − | 0.050 | − |
| | 0.044 | − | 0.065 | − |
| Average of Normal | 0.054 | | 0.051 | |
| Standard deviation | 0.014 | | 0.013 | |
| Cut-off value | 0.082 | | 0.077 | |

TABLE 20

| Classification of symptom | Peptide obtained in Ref. Exam. 1 OD | Judge | Peptide obtained in Ref. Exam. 2 OD | Judge | Peptide obtained in Ref. Exam. 3 OD | Judge |
|---|---|---|---|---|---|---|
| Hepatitis of sporadic | | | | | | |
| 1 acute, acme | 0.054 | − | 0.078 | − | 0.068 | − |
| 2 acute, recovery | 0.056 | − | 0.055 | − | 0.077 | − |
| 3 chronic | 0.036 | − | 0.187 | + | 2.198 | + |
| | 1.323 | + | 0.077 | − | 1.065 | + |
| Hepatitis of post-transfusion | | | | | | |
| 4 acute, acme | 0.076 | + | 0.218 | + | 0.150 | − |
| 5 acute, recovery | 0.054 | − | 0.076 | − | 0.030 | − |
| | 0.046 | − | 0.642 | + | 2.142 | + |
| 6 chronic | 0.044 | − | 0.112 | + | 0.158 | − |
| | 0.060 | − | 0.128 | + | 2.052 | + |
| Alcoholic hepatitis | | | | | | |
| 7 chronic | 0.059 | − | 0.071 | − | 0.057 | − |
| | 0.044 | − | 0.051 | − | 0.029 | − |
| Hepatitis B | | | | | | |
| 8 chronic | 0.051 | − | 0.499 | + | 0.197 | − |
| | 0.040 | − | 0.048 | − | 0.109 | − |
| | 0.042 | − | 0.078 | − | 0.042 | − |
| Normal human serum | | | | | | |
| 9 | 0.051 | − | 0.057 | − | 0.024 | − |
| | 0.051 | − | 0.049 | − | 0.031 | − |
| | 0.077 | + | 0.079 | − | 0.292 | + |
| | 0.059 | − | 0.060 | − | 0.035 | − |
| | 0.052 | − | 0.074 | − | 0.096 | − |
| | 0.060 | − | 0.109 | + | 0.056 | − |
| | 0.049 | − | 0.058 | − | 0.060 | − |
| | 0.053 | − | 0.060 | − | 0.032 | − |
| | 0.063 | − | 0.083 | − | 0.053 | − |
| | 0.045 | − | 0.064 | − | 0.081 | − |
| Average of Normal | 0.056 | | 0.069 | | 0.076 | |
| Standard deviation | 0.009 | | 0.018 | | 0.079 | |
| Cut-off value | 0.074 | | 0.105 | | 0.234 | |

Example 13

Using the peptides obtained in Examples 3, 4 and 5 and Reference Examples 4, 5 and 6, as antigens, the serum specimens listed in Table 18 were examined for anti-HCV antibody by determining the absorbance by enzyme immunoassay in the same manner as in Example 12.

Assay results are given in Tables 21 and 22. The results are given for serum specimens in Table 18 assayed by enzyme immunoassay using the peptides obtained in Examples 3 through 5 in Table 21 and Reference Examples 4 through 6 in Table 22, respectively. Also, a cut-off value was set from the $OD_{492}$ value of 10 specimens of normal human serum, based on which the response to anti-HCV antibody was judged to be positive or negative. The cut-off value was calculated using the equation:

Cut-off value = mean $OD_{492}$ value of normal human serum + 2SD

Results of judgement for positive or negative response obtained on the basis of the cut-off value calculated from the results of normal serum specimens are also given in Tables 21 and 22. It is seen from Table 21 that when the peptides obtained in Examples 3 and 5 were used for enzyme immunoassay, the sera of patients of non-A, non-B acute hepatitis in the recovery stage and the sera patients of non-A, non-B chronic hepatitis were judged to be positive for anti-HCV antibody. The sera of alcoholic hepatitis patients, the sera of hepatitis B patients and the sera of normal subjects were judged to be negative for anti-HCV antibody. The enzyme immunoassay using these peptides proved to be useful in the diagnosis for the patients described above. When the peptide obtained in Example 4 was used for enzyme immunoassay, only the sera of patients of non-A, non-B chronic hepatitis were judged to be positive for anti-HCV antibody; this enzyme immunoassay proved to be useful in the diagnosis for this type of patients. When the peptides obtained in Reference Examples 4 through 6 were used for enzyme immunoassay, some of the sera of patients of diseases listed in Table 18 were judged to be negative for anti-HCV antibody, and in addition, some of the sera of normal subjects were judged to be positive for anti-HCV antibody; therefore, the results of judgement by the enzyme immunoassay using these peptides involved false positive and false negative cases, and the diagnostic efficiency for non-A, non-B hepatitis of the enzyme immunoassay using these peptides proved to be poor. These findings demonstrate that the use of the peptides obtained in Examples 3, 4 and 5 permits efficient judgment for the presence or absence of anti-HCV antibody.

TABLE 21

| Classification of symptom | Peptide obtained in Ref. Exam. 3 OD | Judge | Peptide obtained in Ref. Exam. 4 OD | Judge | Peptide obtained in Ref. Exam. 5 OD | Judge |
|---|---|---|---|---|---|---|
| Hepatitis of sporadic | | | | | | |
| 1 acute, acme | 0.096 | + | 0.058 | − | 0.065 | − |
| 2 acute, recovery | 0.358 | + | 0.636 | + | 0.855 | + |
| 3 chronic | 1.165 | + | 0.065 | − | 1.500 | + |
| | 0.120 | + | 1.352 | + | 1.333 | + |
| Hepatitis of post-transfusion | | | | | | |
| 4 acute, acme | 0.099 | + | 0.080 | + | 0.078 | − |
| 5 acute, recovery | 0.066 | − | 1.256 | + | 0.568 | + |

TABLE 21-continued

| Classification of symptom | Peptide obtained in Ref. Exam. 3 OD | Judge | Peptide obtained in Ref. Exam. 4 OD | Judge | Peptide obtained in Ref. Exam. 5 OD | Judge |
|---|---|---|---|---|---|---|
| | 1.497 | + | 1.420 | + | 1.495 | + |
| 6 chronic | 0.134 | + | 0.182 | + | 0.326 | + |
| | 1.175 | + | 1.939 | + | 1.821 | + |
| Alcoholic hepatitis | | | | | | |
| 7 chronic | 0.186 | − | 0.061 | − | 0.080 | − |
| | 0.043 | − | 0.044 | − | 0.050 | − |
| Hepatitis B | | | | | | |
| 8 chronic | 0.081 | − | 0.059 | − | 0.073 | − |
| | 0.057 | − | 0.041 | − | 0.057 | − |
| | 0.066 | − | 0.053 | − | 0.047 | − |
| Normal human serum | | | | | | |
| 9 | 0.072 | − | 0.050 | − | 0.053 | − |
| | 0.072 | − | 0.060 | − | 0.053 | − |
| | 0.061 | − | 0.053 | − | 0.099 | + |
| | 0.089 | − | 0.064 | − | 0.064 | − |
| | 0.056 | − | 0.056 | − | 0.060 | − |
| | 0.052 | − | 0.050 | − | 0.065 | − |
| | 0.058 | − | 0.051 | − | 0.060 | − |
| | 0.065 | − | 0.060 | − | 0.055 | − |
| | 0.067 | − | 0.069 | − | 0.063 | − |
| | 0.078 | − | 0.064 | − | 0.047 | − |
| Average of Normal | 0.067 | | 0.058 | | 0.062 | |
| Standard deviation | 0.011 | | 0.007 | | 0.014 | |
| Cut-off value | 0.089 | | 0.072 | | 0.090 | |

TABLE 22

| Classification of symptom | Peptide obtained in Ref. Exam. 4 OD | Judge | Peptide obtained in Ref. Exam. 5 OD | Judge | Peptide obtained in Ref. Exam. 6 OD | Judge |
|---|---|---|---|---|---|---|
| Hepatitis of sporadic | | | | | | |
| 1 acute, acme | 0.038 | − | 0.069 | − | 0.061 | − |
| 2 acute, recovery | 0.056 | − | 0.075 | − | 0.060 | − |
| 3 chronic | 0.035 | − | 0.058 | − | 0.078 | − |
| | 0.039 | − | 0.082 | − | 0.084 | + |
| Hepatitis of post-transfusion | | | | | | |
| 4 acute, acme | 0.068 | + | 0.094 | − | 0.071 | − |
| 5 acute, recovery | 0.057 | − | 0.092 | − | 0.306 | + |
| | 0.034 | − | 0.094 | − | 0.076 | − |
| 6 chronic | 0.037 | − | 0.067 | − | 0.103 | + |
| | 0.075 | + | 0.191 | + | 0.078 | − |
| Alcoholic hepatitis | | | | | | |
| 7 chronic | 0.046 | − | 0.069 | − | 0.067 | − |
| | 0.042 | − | 0.053 | − | 0.049 | − |
| Hepatitis B | | | | | | |
| 8 chronic | 0.039 | − | 0.059 | − | 0.086 | + |
| | 0.039 | − | 0.051 | − | 0.043 | − |
| | 0.046 | − | 0.066 | − | 0.280 | + |
| Normal human serum | | | | | | |
| 9 | 0.052 | − | 0.074 | − | 0.047 | − |
| | 0.051 | − | 0.057 | − | 0.045 | − |
| | 0.059 | − | 0.093 | − | 0.066 | − |
| | 0.053 | − | 0.068 | − | 0.059 | − |
| | 0.055 | − | 0.057 | − | 0.056 | − |
| | 0.049 | − | 0.068 | − | 0.083 | + |
| | 0.050 | − | 0.059 | − | 0.045 | − |
| | 0.046 | − | 0.105 | + | 0.051 | − |
| | 0.045 | − | 0.064 | − | 0.068 | − |
| | 0.041 | − | 0.045 | − | 0.055 | − |
| Average of Normal | 0.050 | | 0.069 | | 0.058 | |
| Standard deviation | 0.005 | | 0.018 | | 0.012 | |
| Cut-off value | 0.060 | | 0.105 | | 0.082 | |

Example 14

Using the peptides obtained in Examples 6, 7 and 8 and Reference Example 7, as antigens, the serum specimens listed in Table 18 were examined for anti-HCV antibody by determining the absorbance by enzyme immunoassay in the same manner as in Example 12.

Assay results are given in Table 23. The results are given for serum specimens in Table 18 assayed by enzyme immunoassay using the peptides obtained in Examples 6 through 8 and Reference Example 7, respectively. Also, a cut-off value was set from the $OD_{492}$ value of 10 specimens of normal human serum, based on which the response to anti-HCV antibody was judged to be positive or negative. The cut-off value was calculated using the equation:

Cut-off value = mean $OD_{492}$ value of normal human serum + 2SD

Results of judgement for positive or negative response obtained on the basis of the cut-off value calculated from the results of normal serum specimens listed in Table 23 are also given in Table 23. It is seen from Table 23 that when the peptides obtained in Example 6 were used for enzyme immunoassay, the sera of patients of non-A, non-B chronic hepatitis of sporadic were judged to be positive and the sera of patients of acute and in the recovery stage of PTNANBH and chronic hepatitis were judged to be positive for anti-HCV antibody. The sera of alcoholic hepatitis patients, the sera of hepatitis B patients and the sera of normal subjects were judged to be negative for anti-HCV antibody. The enzyme immunoassay using these peptides obtained in Example 6 proved to be useful in the early diagnosis for the patients of non-A, non-B hepatitis. When the peptide obtained in Examples 7 and 8 were used for enzyme immunoassay, the sera of patients of non-A, non-B chronic hepatitis in the recovery stage and the sera of patients of chronic hepatitis were judged to be positive for anti-HCV antibody; this enzyme immunoassay proved to be useful in the diagnosis for this type of patients. When the peptides obtained in Reference Example 7 were used for enzyme immunoassay, every sera of patients of non-A, non-B hepatitis were judged to be negative for anti-HCV antibody, and in addition, some of the sera of patients of alcoholic hepatitis and hepatitis B were incidentaly judged to be positive for anti-HCV antibody; therefore, the results of judgment by the enzyme immunoassay using these peptides obtained in Reference Example 7 involved false negative and false positive cases, and the diagnostic efficiency for non-A, non-B hepatitis of the enzyme immunoassay using these peptides proved to be poor. These findings demonstrate that the use of the peptides obtained in Examples 6, 7 and 8 permits efficient judgment for the presence or absence of anti-HCV antibody.

TABLE 23

| | Example No. of peptide obtained | | | | | | | |
|---|---|---|---|---|---|---|---|---|
| | Example 6 | | Example 7 | | Example 8 | | Ref. Exam. 7 | |
| Classification of symptom | OD | Judge | OD | Judge | OD | Judge | OD | Judge |
| Hepatitis of | | | | | | | | |

TABLE 23-continued

| | Example No. of peptide obtained | | | | | | | |
|---|---|---|---|---|---|---|---|---|
| | Example 6 | | Example 7 | | Example 8 | | Ref. Exam. 7 | |
| Classification of symptom | OD | Judge | OD | Judge | OD | Judge | OD | Judge |
| sporadic | | | | | | | | |
| 1 acute, acme | 0.075 | + | 0.049 | — | 0.092 | — | 0.058 | — |
| 2 acute, recovery | 0.935 | + | 1.631 | + | 0.308 | + | 0.073 | — |
| 3 chronic | 1.703 | + | 0.038 | — | 0.104 | — | 0.046 | — |
| Hepatitis of post-transfusion | | | | | | | | |
| 4 acute, acme | 0.077 | + | 0.110 | + | 0.194 | + | 0.085 | — |
| 5 acute, recovery | 0.949 | + | 0.071 | — | 0.205 | + | 0.082 | — |
| | 1.504 | + | 0.061 | — | 0.063 | — | 0.070 | — |
| 6 chronic | 1.174 | + | 0.112 | + | 0.102 | — | 0.078 | — |
| | 2.116 | + | 2.106 | + | 1.696 | + | 0.105 | + |
| Alcoholic hepatitis | | | | | | | | |
| 7 chronic | 0.057 | — | 0.923 | + | 0.074 | — | 0.091 | + |
| | 0.060 | — | 0.064 | — | 0.045 | — | 0.091 | + |
| Hepatitis B | | | | | | | | |
| 8 chronic | 0.071 | — | 0.065 | — | 0.075 | — | 0.077 | — |
| | 0.055 | — | 0.052 | — | 0.077 | — | 0.064 | — |
| | 0.069 | — | 0.107 | + | 0.067 | — | 0.099 | + |
| Normal human serum | | | | | | | | |
| 9 | 0.051 | — | 0.054 | — | 0.047 | — | 0.062 | — |
| | 0.062 | — | 0.051 | — | 0.079 | — | 0.057 | — |
| | 0.068 | — | 0.067 | — | 0.063 | — | 0.075 | — |
| | 0.052 | — | 0.074 | — | 0.143 | — | 0.077 | — |
| | 0.060 | — | 0.059 | — | 0.183 | + | 0.079 | — |
| | 0.063 | — | 0.058 | — | 0.055 | — | 0.070 | — |
| | 0.061 | — | 0.060 | — | 0.051 | — | 0.071 | — |
| | 0.063 | — | 0.060 | — | 0.073 | — | 0.068 | — |
| | 0.065 | — | 0.070 | — | 0.059 | — | 0.080 | — |
| | 0.050 | — | 0.051 | — | 0.064 | — | 0.064 | — |
| Average of Normal | 0.060 | | 0.060 | | 0.082 | | 0.070 | |
| Standard deviation | 0.006 | | 0.008 | | 0.045 | | 0.008 | |
| Cut-off value | 0.072 | | 0.076 | | 0.171 | | 0.086 | |

Example 15

Subject samples

Blood donor serum: 2476 specimens
Determination by enzyme immunoassay

Each serum specimen was examined for anti-HCV antibody by determining the absorbance by the following enzyme immunoassay procedure.

Specifically, each peptide obtained in Example 1, as the antigen, was dissolved in 0.01M carbonate buffer (pH 9.5). The resulting peptide solution was added to polystyrene enzyme immunoassay cups (product of Dynatech Laboratories Incorporation) at 100 μl per cup and kept standing at 4° C. for 12 hours for peptide coating. Then, these cups were washed with three portions of PBS containing 0.05% by volume of Tween 20. Subsequently, 150 μl of PBS containing 20% by volume of normal goat serum was added to each cup, and the cup was kept standing at room temperature for 3 hours to block the nonspecific protein binding site. Then, after removing the PBS containing 20% by volume of normal goat serum used for blocking, each assay cup was dried.

After adding 100 μl of PBS containing 10% by volume of normal goat serum, as the serum diluent, to each assay cup described above, each subject serum was added so that the ratio of the serum diluent to the subject serum became 20 to 1 (by volume). After incubation at 37° C. for 1 hour, these cups were washed with three portions of PBS containing 0.05% by volume of Tween 20.

To each assay cup thus treated, 100 μl of a goat anti-human IgG antibody-peroxidase conjugate (diluted to an optimum concentration with PBS containing 10% by volume of normal goat serum) was added. After incubation at 37° C. for 30 minutes, these cups were washed with three portions of PBS containing 0.05% by volume of Tween 20. Subsequently, to each assay cup thus treated, 100 μl of a coloring agent (prepared by dissolving o-phenylenediamine in a 0.1M citrate-phoasphate buffer, pH 5.6, containing 0.02% by volume of hydrogen peroxide, to a final concentration of 0.3% by weight) was added. After the mixture was kept standing at room temperature for 15 minutes, 100 μl of 2N sulfuric acid was added to stop the reaction, and the absorbance at 492 nm ($OD_{492}$) of the reaction mixture was determined.

Results

A cut-off value was set from the results of an inhibition test for anti-HCV antibody using the peptide obtained in Example 1. Table 24 gives the results of judgment based on the results descried above wherein the specimens exceeding 0.5 in $OD_{492}$ value were judged to be positive for anti-HCV antibody and those below 0.5 were judged to be negative. Table 24 also gives the results of judgement by EIA and RIBA using a commercial anti-HCV antibody assay reagent (product of Ortho Diagnostic Systems Inc.) on the 2476 specimens of blood donor serum described above.

TABLE 24

| | Judgement of anti-HCV antibody using peptide obtained in Example 1 | | |
|---|---|---|---|
| | + | — | Total |
| Judgement by EIA and RIBA using commercial anti-HCV antibody assay reagent | | | |
| + | 14 (0.6%) | 0 (0.0%) | 14 (0.6%) |
| — | 35 (1.4%) | 2427 (98.0%) | 2462 (99.4%) |
| Total | 49 (2.0%) | 2427 (98.0%) | 2476 (100.0%) |

As is evident from Table 24, of the 2462 specimens judged to be negative using the commercial anti-HCV antibody assay reagent, 35 were judged to be positive for anti-HCV antibody when the peptide obtained in Example 1 was used. Also, the 14 specimens judged to be positive using the commercial anti-HCV antibody assay reagent were all judged to be positive for anti-HCV antibody when the peptide obtained in Example 1 was used.

---

What is claimed is:

1. A peptide consisting of an amino acid sequence of the formula (I):

H—Lys Asp Arg Thr Gln Gln Arg Lys Thr Lys Arg Ser Thr Asn Arg Arg Ser Lys Asn Glu Lys Lys Lys Lys—OH (SEQ ID NO: 1).

2. An antibody assay reagent for a non-A, non-B hepatitis associated antigen, having the peptide of claim 1.

* * * * *